US008513267B2

(12) United States Patent
Franchini et al.

(10) Patent No.: US 8,513,267 B2
(45) Date of Patent: Aug. 20, 2013

(54) 4-ANILINOQUINAZOLINE DERIVATIVES WITH ADENOSINE-KINASE INHIBITOR PROPERTIES

(75) Inventors: Kleber Gomes Franchini, Campinas (BR); Mario Jose Abdalla Saad, Campinas (BR); Roberto Rittner Neto, Campinas (BR); Rodrigo Miguel Marin, Campinas (BR); Silvana Aparecida Rocco, Campinas (BR)

(73) Assignee: Universidade Estadual de Campinas-Unicamp, Campinas-SP (BR)

( * ) Notice: Subject to any disclaimer, the term of this patent is extended or adjusted under 35 U.S.C. 154(b) by 1641 days.

(21) Appl. No.: 11/515,514

(22) Filed: Sep. 1, 2006

(65) Prior Publication Data
US 2007/0060600 A1 Mar. 15, 2007

Related U.S. Application Data

(63) Continuation of application No. PCT/BR2004/000196, filed on Oct. 7, 2004.

(30) Foreign Application Priority Data
Feb. 3, 2004 (BR) ...................................... 0400869

(51) Int. Cl.
*A01N 43/54* (2006.01)
*A61K 31/517* (2006.01)
*C07D 239/72* (2006.01)
*C07D 401/00* (2006.01)

(52) U.S. Cl.
USPC .......................... 514/266.1; 544/283; 544/284

(58) Field of Classification Search
USPC ................ 514/266.4, 266.1, 266.2; 544/293, 544/283, 284
See application file for complete search history.

(56) References Cited

U.S. PATENT DOCUMENTS

| 5,409,930 | A | 4/1995 | Spada et al. |
| 5,457,105 | A | 10/1995 | Barker |
| 5,480,883 | A | 1/1996 | Spada et al. |
| 5,616,582 | A | 4/1997 | Barker |
| 5,646,128 | A | 7/1997 | Firestein et al. |
| 5,646,153 | A | 7/1997 | Spada et al. |
| 5,658,889 | A | 8/1997 | Gruber et al. |
| 5,674,998 | A | 10/1997 | Boyer et al. |
| 5,710,158 | A | 1/1998 | Myers et al. |
| 5,714,493 | A | 2/1998 | Myers et al. |
| 5,721,237 | A | 2/1998 | Myers et al. |
| 5,721,356 | A | 2/1998 | Ugarkar et al. |
| 5,726,302 | A | 3/1998 | Ugarkar et al. |
| 5,763,596 | A | 6/1998 | Boyer et al. |
| 5,763,597 | A | 6/1998 | Ugarkar et al. |
| 5,795,889 | A | 8/1998 | Spada et al. |
| 5,795,977 | A | 8/1998 | Ugarkar et al. |
| 5,864,033 | A | 1/1999 | Browne et al. |
| RE36,256 | E | 7/1999 | Spada et al. |
| 6,057,320 | A | 5/2000 | Spada et al. |
| 6,258,820 | B1 | 7/2001 | Uckun et al. |
| RE37,650 | E | 4/2002 | Myers et al. |
| 6,593,333 | B1 | 7/2003 | Cumming |
| 6,645,969 | B1 | 11/2003 | Myers et al. |
| 7,081,461 | B1 * | 7/2006 | Mortlock et al. ........ 514/266.31 |
| 2001/0016588 | A1 | 8/2001 | Uckun et al. |
| 2002/0137757 | A1 | 9/2002 | Uckun et al. |
| 2003/0216417 | A1 | 11/2003 | Cumming |
| 2004/0014774 | A1 | 1/2004 | Myers et al. |
| 2004/0039002 | A1 | 2/2004 | Uckun et al. |

FOREIGN PATENT DOCUMENTS

| EP | 0 566 226 | 10/1993 |
| WO | WO 92/12718 | 8/1992 |
| WO | WO 92/20642 | 11/1992 |
| WO | WO 95/15758 | 6/1995 |
| WO | WO 96/40706 | 12/1996 |
| WO | WO 00/20402 | 4/2000 |
| WO | WO 00/23444 | 4/2000 |
| WO | WO 00/56720 | 9/2000 |
| WO | WO 2004/013091 | 2/2004 |
| WO | WO 2005/085213 | 9/2005 |

OTHER PUBLICATIONS

PCT International Search Report, PCT/BR2004/000196, dated Feb. 15, 2005.
Fredriksson et al., "In vivo evaluation of the biodistribution of 1 1C-labeled PD153035 in rats without and with neuroblastoma implants," Life Science, 1999, pp. 165-174, vol. 65, No. 2.
Cronstein, B. N., "Adenosine, an endogenous anti-inflammatory agent," J. Appl. Physiol., vol. 76, pp. 5-13 (1994).
Muchmore, S. W., et al., "Crystal Structures of Human Adenosine Kinase Inhibitor Complexes Reveal Two Distinct Binding Modes," J. Med. Chem, vol. 49, pp. 6726-6731 (2006).
Tatlisumak, T., et al., "Delayed Treatment With an Adenosine Kinase Inhibitor, GP683, Attenuates Infarct Size in Rats With Temporary Middle Cerebral Artery Occlusion," Stroke, J. Amer. Heart Assoc., vol. 29, pp. 1952-1958 (1998).

(Continued)

*Primary Examiner* — Paul V. Ward
(74) *Attorney, Agent, or Firm* — Birch, Stewart, Kolasch & Birch, LLP.

(57) ABSTRACT

The present invention relates to the use of 4-anilinoquinazoline derivatives as adenosine-kinase inhibitors. The present invention also relates to a method for protecting tissues and organs like heart, brain and kidneys affected by ischemia, and for treating heart insufficiency, myocardium infarct, arrhythmia, arterial hypertension, atherosclerosis, coronary artery restenosis after angioplasty, chronic renal insufficiency, cerebral vascular accident, and chronic inflanunatory diseases (e.g., rheumatoid arthritis). The present invention also relates to the compound 6,7-dimethoxy-4-(3'-N',N'-dimethylaminoanilino)quinazoline, or a pharmaceutically acceptable salt thereof, pharmaceutical composition comprising it and use of such compound in the manufacture of a medicament for treating or preventing diseases or conditions that are benefited from the adenosine-kinase inhibition.

7 Claims, 9 Drawing Sheets

(56) References Cited

OTHER PUBLICATIONS

Jarvis, M. F., et al., "ABT-702 (4-Amino-5-(3-bromophenyl)-7-(6-morpholino-pyridin-3-yl)pyrido[2,3d]pyrimidine), a Novel Orally Effective Adenosine Kinase Inhibitor with Analgesic and Anti-Inflammatory Properties: I. In Vitro Chracterization and Acute Antinociceptive Effects in the Mouse," J. Pharma. & Experim. Therapeutics, vol. 295, No. 3, pp. 1156-1164 (2000).

Maj, M. C., "Structure-Activity Studies on Mammalian Adenosine Kinase," Biochem. & Biophys. Res. Comm., vol. 275, pp. 386-393 (2000).

McNally, T., et al., "Cloning and Expression of the Adenosine Kinase Gene from Rat and Human Tissues," Biochem. and Biophys. Res. Comm., vol. 231, pp. 645-650 (1997).

Cronstein, B. N., et al., "Adenosine: an Endogenous Inhibitor of Neutrophil-mediated Injury to Endothelial Cells," J. Clin. Invest., vol. 78, pp. 760-770 (1986).

Dubey, R. K., et al., "$A_{2B}$ Receptors Mediate Antimitogenesis in Vascular Smooth Muscle Cells," Hypertension, J. Amer. Heart Assoc., vol. 35, pp. 267-272 (2000).

Bauer, C., et al., "Adenosine kinase inhibitor GP515 attenuates hepatic leukocyte adhesion after hemorrhagic hypotension," Am. J. Physiol. Gastrointest. Liver Physiol., vol. 273, pp. 1297-1303 (1997).

Harada, N., et al., "Adenosine and Selective $A_{2A}$ Receptor Agonists Reduce Ischemia/Reperfusion Injury of Rat Liver Mainly by Inhibiting Leukocyte Activation," J. Pharm. Exp. Therap., vol. 294, No. 3, pp. 1034-1042 (2000).

Peralta, C., et al., "The Protective Role of Adenosine in Inducing Nitric Oxide Synthesis in Rat Liver Ischemia Preconditioning Is mediated by Activation of Adenosine $A_2$ Receptors," Hepatology, vol. 29, pp. 126-132 (1999).

Firestein, G. S., et al., "Protective Effect of an Adenosine Kinase Inhibitor in Septic Shock," J. Immunol., vol. 152, pp. 5853-5859, (1994).

Lee, H. T., et al., "$A_1$ Adenosine Receptor Activation Inhibits Inflammation, Necrosis, and Apoptosis after Renal Ischemia-Reperfusion Injury in Mice," J. Am. Soc. Nephrol., vol. 15, pp. 102-111 (2004).

Shewchuk, L., et al., "Binding Mode of the 4-Anilinoquinazoline Class of Protein Kinase Inhibitor: X-ray Crystallographic Studies of 4-Anilinoquinazolines Bound to Cyclin-Dependent Kinase 2 and p38 Kinase," J. Med. Chem., vol. 43, pp. 133-138 (2000).

Britton, D. R., et al., "Site and event specific increase of striatal adenosine release by adenosine kinase inhibition in rats," Neurosci Lett. vol. 266, pp. 93-96 (1999).

\* cited by examiner

Z = CO$_2$H, CO$_2$R, C(O)NH$_2$, CN

R$_1$ = H, alkyl; R$_2$ = substituent to be chosen; R$_3$ = H, alkyl.

a: formamide, formamide acetate etc.

b: POCl$_3$ or SOCl$_2$/DMF c: ArNH$_2$ d: P$_2$S$_5$ e: R$_3$I, base

3- Chromatogram of the control 2

Det fluor (Ex: 27nm, Em:410)

| Pk# | Name | Retention Time | Area | ESTD concentration | Normalized Conc. |
|---|---|---|---|---|---|
| 1 | ado | 4.489 | 2488452 | 0.863 | 0.478 nmol/mg |
| 2 | amp | 5.728 | 10275590 | 134.947 | 74.7 nmol/mg |

4- Chromatogram of the treated sample

Det fluor (Ex: 27nm, Em:410)

| Pk# | Name | Retention Time | Area | ESTD concentration | Normalized Conc. |
|---|---|---|---|---|---|
| 1 | ado | 4.372 | 2814586 | 0.976 | 0.75 nmol/mg |
| 2 | amp | 5.577 | 7916092 | 103.960 | 79.62 nmol/mg |

Legend:

ADO = Adenosine;
Inhibitor = 8-Phenylteophylin

4-ANILINOQUINAZOLINE DERIVATIVES WITH ADENOSINE-KINASE INHIBITOR PROPERTIES

CROSS-REFERENCE TO RELATED APPLICATIONS

This application is a continuation of PCT International Patent Application PCT/BR2004/000196, filed Oct. 7, 2004, designating the United States of America, and published, in English, as International Patent Publication No. WO 2005/085213 A1 on Sep. 15, 2005, which claims the benefit under 35 U.S.C. §119 of Brazilian Patent Application Ser. No. PI 0400869-3, filed Mar. 2, 2004, the contents of the entirety of each of which is incorporated by this reference.

FIELD OF THE INVENTION

This invention relates to compounds derived from 4-anilinoquinazolines that present adenosine-kinase inhibitory activity and use thereof in diseases or conditions that are benefited from the adenosine kinase inhibition. More particularly, the present invention relates to the compound 6,7-dimethoxy-4-(3'-N',N'-dimethylaminoanilino)quinazoline, or a pharmaceutically acceptable salt thereof, pharmaceutical composition comprising it and the use of the adenosine kinase inhibitory properties of the compound for protecting tissues and organs like heart, brain and kidneys affected by ischemia, and for treating heart insufficiency, myocardium infarct, hypertension, atherosclerosis, coronary restenosis after angioplasty, chronic kidney insufficiency, cerebral vascular accident, chronic inflammatory diseases (e.g., rheumatoid arthritis).

BACKGROUND OF THE INVENTION

The compounds included in the present invention are quinazoline derivatives previously described as inhibitors of tyrosine kinase from the family of EGF receptors (Fry et al., *Science* 1994, 265, 1093; and Patents No. BR9708640 and EP 566226), now they are unexpectedly found as inhibitors of adenosine kinase.

For a better comprehension of the present invention, some known compounds and their properties are defined and described, together with specific terms related to this invention.

Adenosine. Adenosine is a purinic nucleoside that regulates multiple cell functions, and its effects are mediated by at least four kinds of P1 purinergic receptors located in cell membranes of almost all kinds of cells, namely A1, $A_{2a}$, $A_{2b}$ and A3 (Fredholm et al., *Pharmacol. Rev.* 2001, 53:527). Despite acting in practically in all cells and organs of the organism, its main effects are observed in the heart, brain, kidneys and immune system cells. Because its action is restricted to the site where it is released, adenosine is considered an autacoid (form the Greek autos—self and akos—relief, cure). In general, its complex effects result in reduction of metabolic activity and protection against physiological and pathological stimuli associated to sustained increases of cell activity. Its protective effects are well known for ischemia/reperfusion deleterious actions, pro-inflammatory substances, as well as its effects as analgesic, modulator of neuronal activity related to sleep, sympatholitic, inhibitor of thrombosis aggregation, inhibitor of neutrophilic adhesion, inhibitor of free radical production and vasodilator.

Pharmacological inhibitors of the adenosine catabolism. Considering its wide range of effects, there is no surprise in the rising interests in the therapeutic usage of adenosine, its mimetics and in substances that interfere in its metabolism and bioavailability. The usage of adenosine itself as a therapeutic agent is restricted due to its short half-life (estimated in less than one second in circulation) and its undesirable hemodynamic effects. These arguments are also valid for agonists and antagonists of receptor that like adenosine may have undesirable systemic effects. However, approaches that interfere in local metabolism and bioavailability of adenosine are promising. In this case, it should be noticed that adenosine is formed mainly as a result of the action of intra and extra-cellular 5'-nucleotidases that dephosphorylate 5'-AMP, and of the SAH-hydrolase on the S-adenosyl-homocysteinee (SAH) (Headrick et al., *Am. J. Physiol. Heart Circ. Physiol.* 2003, 285:H1797). Otherwise, extra-cellular adenosine is quickly absorbed by cells through a specific membrane carrier. In the intracellular environment, adenosine is deaminated turning into inosine, by adenosine deaminase or re-phosphorylated into 5'-AMP by adenosine kinase. The high catabolism, besides the high membrane transport speed, determines that adenosine has a short half-life and highly localized physiological functions. The importance of these mechanisms for local adenosine bioavailability is confirmed by the increase in tissue concentration caused by inhibitors of membrane carriers of adenosine, as well as by the action activity inhibitors of adenosine kinase or deaminase (Headrick et al., *Am. J. Physiol. Heart Circ. Physiol.* 2003, 285:H1797; and Kowaluk and Jarvis, *Expert Opin. Investig. Drugs* 2000, 9:551). In this case of enzyme inhibitors, available evidences suggest a potential utility for the therapy of clinical situations, where deleterious effects of ischemia/reperfusion, inflammation and pain are involved.

Adenosine Kinase. Adenosine kinase, also known as adenosine 5'-phosphotransferase, is the most abundant nucleoside kinase in mammals, and catalyzes the phosphorylation of the 5'-hydroxyl of the ribofuranosyl of nucleoside analogs, using ATP or GTP as phosphate donor. The structures of adenosine kinases from different species, including human, have been determined, obtained from the placenta. The enzyme is a monomer, whose structure consists of a large $\alpha/\beta$ dominion with nine $\beta$-bands and eight $\alpha$-helixes and a smaller $\alpha/\beta$ dominion with five $\beta$-bands and two $\alpha$-helixes (Mathews et al., *Biochemistry* 1998, 37:15607). The active site is located along the edge of the $\beta$-band in the larger $\alpha/\beta$ dominion, and this is where adenosine attaches itself, while the smaller $\alpha/\beta$ dominion blocks the upper face of the active site, and another nearby site receives the ATP. A magnesium binding site is located between binding sites of adenosine and ATP, and this is an essential ion for the catalysis of adenosine kinase. The model proposed for the activity of this kinase suggests that the amino acid aspartate, located in the position 300, is an important catalytic remainder involved in the deprotonation of the 5'-hydroxyl group during phosphate transfer.

The pharmacological inhibition of adenosine kinase has been described with adenosine analogs (e.g., aminoadenosine and iodotubercidine), as well as with pyridopyrimidine derivatives (Kowart et al., *Bioorg. Med. Chem. Lett.* 2001, 11:83; Lee et al., *J. Med. Chem.* 2001, 44:2133; Zheng et al., *Bioorg. Med. Chem. Lett.* 2001, 11:2071; Gomitsian et al., *J. Med. Chem.* 2002, 45:3639; Gfesser et al., *Eur. J. Med. Chem.* 2003, 38:245; Zheng et al., *Bioorg. Med. Chem. Lett.* 2003, 13:3041; and Perner et al., *J. Med. Chem.* 2003, 46:5249). Studies of therapeutic application of these compounds have shown beneficial effects of inhibition of the adenosine kinase in situations of myocardium ischemia, pain and inflammatory processes (Jarvis et al., *Pain* 2002, 96:107; Suzuki et al., *Br. J.*

*Pharmacol.* 2001, 132:1615; Boyle et al., *J. Pharmacol. Exp. Ther.* 2001, 296:495; Kowaluk et al., *J. Pharmacol. Exp. Ther.* 2000, 295:1165; Jarvis et al., *J. Pharmacol. Exp. Ther.* 2000, 295:1156; and Smolenski et al., *Circulation* 2001, 104(suppl I):I-246).

Ischemia/Reperfusion. Ischemia, defined as improper blood supply to tissues and organs, is one of the main causes of death and disability in populations all over the world, and its main determinant is the atherosclerotic disease of arteries. Its effects in the heart, brain or kidneys are caused mainly by the lack of oxygen, which leads to, depending on intensity and duration, to death or cell degeneration, resulting in different clinical situations like myocardium infarct, chest angina, heart insufficiency, brain vascular accident and kidney insufficiency. Otherwise, an additional deleterious effect is caused after restoration of blood flow in the ischemic area, a condition that many times occurs spontaneously or by therapeutic interference (e.g., coronary thrombosis). Mechanisms that cause deleterious effects of reperfusion are poorly known. Nevertheless, important pathogenic agents considered are the massive oxy radicals generation and the overload of intracellular calcium due to reperfusion. Therefore, tissue lesions caused by ischemia are frequently a consequence of a combination of deleterious effects of the ischemia per se and of reperfusion. We should include in the context lesions to organs (e.g., heart, kidney and liver) used in transplantations.

Surely, the obvious solution to the morbid-mortality caused by conditions of ischemia in several organs is the prevention of atherosclerotic disease. However, the impact of available strategies for primary prevention is still very limited. Therefore, effective prevention ways are needed and, particularly, therapeutic ways to limit the extension of tissue lesions caused by ischemia, and the preservation of the viability of ischemic tissues is one of the most imperious present therapeutic objectives.

In this context, it is important to mention that cells from multicellular organisms have a self-protection mechanism for the lesion by ischemia/reperfusion, activated by repeated events of sub-lethal ischemia, known as ischemic pre-conditioning (Yellon and Downey, *Physiol. Rev.* 2003, 83:1113). This mechanism has two ways of protection: one known as "classical" that last about two hours after the conditioning ischemia, followed after about 24 hours by a second protection window that lasts three days, known as "late protection." The current model for explaining preconditioning states that conditioning ischemia causes the release of various autacoids that trigger the protection process through the activation of membrane receptors (Yellon and Downey, *Physiol. Rev.* 2003, 83:1113). This activation triggers the combination of complex cell signaling ways that during lethal ischemia converge to one or more effectors to mediate protection. The effectors of this response are still poorly known. Nevertheless, in the therapeutic point-of-view, it is important that pharmacological agents that activate signaling ways at different levels may mimic the conditioning stimulus, leading to the expectation that pharmacological agents may be produced in order to explore therapeutically the powerful tissue protection activated by endogenous mechanisms responsible to ischemic pre-conditioning.

Thus, it is known that adenosine is the main triggering agent in the activation of cell ways involved in the classical or late pre-conditioning (Headrick et al., *Am. J. Physiol. Heart Circ. Physiol.* 2003, 285:H1797). Consistent results from clinical studies point out benefits of the use of adenosine for the preservation of the ischemic myocardium, but clinical evidences are still scarce for its therapeutic effect in brain and kidney ischemic lesions, yet it does not mean that it is not effective. It has been demonstrated, for instance, that its action restores ATP stocks in endothelium cells and myocytes, inhibits the formation of free radicals, inhibits the accumulation and the activity of neutrophils, and improves microcirculation (Mahaffey et al., *J. Am. Col. Cardiol.* 1999, 34:1711). Additionally, because adenosine is the main endogenous agent that activates ischemic pre-conditioning, its effect is particularly important in acute coronary syndromes, for they are usually caused by dynamic coronary occlusion with intermittent blood flow periods, having a potential deleterious effect due to the ischemia/reperfusion mechanism. In models of acute coronary syndrome in experimental animals, adenosine reduces consistently the size of the infarct, improves ventricular function and improves coronary flow (Yellon and Downey, *Physiol. Rev.* 2003, 83:1113; and Headrick et al., *Am. J. Physiol. Heart Circ. Physiol.* 2003, 285: H1797). Clinical studies demonstrated that adenosine administration reduces the extension of myocardium infarcts, improves the conditions of myocardium flow, reduces the incidence of heart insufficiency and of myocardium infarct with Q wave in patients submitted to primary angioplasty, also reduces variation of the segment S-T, lactate production and ischemic symptoms in patients submitted to elective angioplasty (Mahaffey et al., *J. Am. Col. Cardiol.* 1999, 34:1711). Recently, results from the study AMISTAD (Acute Myocardial Infarction Study of Adenosine), planned to test the hypothesis that adenosine reduces the size of myocardium infarct in patients submitted to thrombolysis, demonstrated reduction in sizes of previous infarcts in patients treated with adenosine (Mahaffey et al., *J. Am. Col. Cardiol.* 1999, 34:1711). However, no differences between the clinical evolution of treated and non-treated patients was observed. The absence of measurable clinical benefits with adenosine in this study reflects problems with biases in choice of patient groups, but also pharmacokinetic and pharmacodynamic problems of adenosine, as well as its short half-life and undesirable hemodynamic effects.

Therefore, it is possible that pharmacological agents that modify local adenosine bioavailability show to be effective for the protection of the myocardium and other tissues submitted to ischemia/reperfusion.

Inflammation. Chronic inflammatory diseases represent a wide range of diseases that attack organs and tissues in different ways and extensions. In this group, one may include, among others, asthma, rheumatoid arthritis, inflammatory diseases of the intestine, psoriasis and atherosclerosis (Barnes and Karim, *N. Engl. J. Med.* 1997, 336:1066; and Ross, *N. Engl. J. Med.* 1999, 340:115). In spite of representing different physiopathological situations, all inflammatory diseases present the activation and collapse of the immune system responsible for the amplification and support of the inflammatory process. Causes of these diseases remain unknown, but there is little doubt that the pathological process results from the interaction between genetic and environmental factors. Genes, like those in asthma atopy, HLA antigens in rheumatoid arthritis and intestine inflammatory diseases, may determine the susceptibility of patients to the disease, but frequently unknown environmental factors may determine clinical presentation and course. Once established, the chronic inflammatory process develops itself alone. Anti-inflammatory agents and immunosuppressors may suppress the vicious circle, but there is still no healing treatment for any chronic inflammatory diseases.

Deleterious effects of chronic inflammatory processes occur through several mechanisms, but main determinants are local production of pro-inflammatory cytokines and transformation of tissue inflammatory cells in autonomous lineages. These transformations and cytokine production are processes regulated by complex signaling ways that involve many transduction elements and transcription factors. Nevertheless, one transcription factor, NF-κB, seems to be a key element for the activation and transformation of tissue inflammatory cells (Barnes and Karim, *N. Engl. J. Med.* 1997, 336:1066; and Lawrence et al., *Nat. Med.* 2001, 7:1291). This factor is related to the expression of genes responsible for adhesion and recruitment of circulation inflammatory cells (e.g., neutrophils, eosinophils and T lymphocytes) in inflammatory sites, as well as for cytokine and enzyme production in chronic inflammatory diseases. One of these genes is the inducible NOS, whose expression in increased in the epithelium of aerial ways cells and macrophages of asthma patients, in colon epithelium of ulcerative colitis patients and in synovial cells of inflamed joints. The cyclooxygenase-2, another inducible enzyme regulated by NF-κB, is responsible by the increase in prostaglandin and tromboxane production in inflammatory diseases. On the other hand, the production of interleukin-1β, TNF-α, interleukin-6, stimulant factor of granulocyte/macrophage colonies, and many chemotactic cytokines is increased in patients of asthma, rheumatoid arthritis, psoriasis and intestine inflammatory disease. All these cytokines have an important role in these inflammatory processes. Interleukin-1β and TNF-α may influence the severity of these diseases, possibly by permanently activating NF-κB. The treatment of rheumatoid arthritis patients with drugs that block the action of TNF-α may control the disease.

Adenosine is an endogenous immunomodulator with antiinflammatory and immunosuppressor properties, which acts through multiple mechanisms still not completely established. Some evidences point out that adenosine inhibits the activation of NF-κB that is induced by TNF, what may contribute for its role in the suppression of inflammations and immunomodulation (Kowaluk et al., *J. Pharmacol. Exp. Ther.* 2000, 295:1165; and Jarvis et al., *J. Pharmacol. Exp. Ther.* 2000, 295:1156). Therefore, the use of adenosine kinase inhibitors may present therapeutic benefits to a wide range of clinical situations directly or indirectly dependent of inflammatory and immunological processes. Among conditions that could benefit from the use of adenosine kinase are chronic degenerative inflammatory diseases (e.g., rheumatoid arthritis, systemic erythematous lupus etc.), asthma, atherosclerosis, ulcerative colitis, and Chron disease.

Pain. Chronic or acute pain are among most frequent clinical conditions. Mechanisms involved in its beginning and sustenance are multiple and comprise from neuronal degeneration to inflammation. Pain initiator stimuli are transmitted to the central nervous system by the activation of non-myelinized (C fibers) and myelinized (Aδ fibers) afferents. Cell bodies of these fibers are located in the dorsal root, trigeminal ganglion, and nodous ganglion. These fibers establish multiple connections with the spinal medulla or cerebral trunk, and with specific areas of the prosencephalon, where the stimulus is integrated. Following the tissue lesion or the inflammation, a large number of endogenous substances are released, and these substances may activate or sensibilize nociceptor afferents. These substances comprise $H^+$, ATP, bradikinine, 5-HT, histamine, prostaglandins, P substance and adenosine (Bevan, 1999, In: P. D. Wall and R. Melzack (Eds.), *Textbook of Pain, fourth ed.* Churchill Livingstone, Edinburgh, pp. 85-103). Some of these mediators act through binders associated to cationic channels (e.g., $H^+$, ATP, 5-$HT_3$), while others act through G-protein-coupled receptors (GPCRs) (e.g., prostaglandins, bradikinines, 5-HT). Changes in the excitability of nociceptor afferents may result from the activation of multiple intracellular signaling ways mediated by kinase proteins with subsequent phosphorylation of specific sodium channels of sensorial neurons. There are three basic therapeutic approaches for controlling pain: (1) suppression of the source, (2) change in central perception, and (3) transmission blocking for the central nervous system.

Adenosine and its analogs have analgesic effect. Their actions are complex and multiple, including action in central and peripheral mechanisms. Thus, spinal administration of adenosine or its analogs (e.g., 5'-N-ethyl-carboxamidoadenosine (NECA)) produces analgesia through an effect mediated by A1 receptors, whose activation produces liberation inhibition of nociceptive afferents CGRP (Mauborgne et al., *Eur. J. Pharmacol.* 2002, 441:47). Likewise, the same effect has been demonstrated for adenosine metabolism inhibitors (Sawynok, *Curr. Opin. Cent. Periph. Nerv. Syst. Invest. Drugs* 1999, 1:27; and Kowaluk et al., *Exp. Opin. Invest. Drugs* 2000, 9:551). The inhibition of adenosine kinase with 5'-amino-5'-deoxyadenosine or iodotubercidine increase the bioavailability of adenosine in the spinal medulla (Golembiowska et al., *Brain Res.* 1995, 699:315).

Adenosine acts also directly on peripheral nerves by interfering in the process of nociceptor activation, through complex mechanisms. Its actions may result in inhibition or increase of pain through the action on nociceptor afferents via A1 and A2A receptors, and it results from the reduction or increase of cAMP, respectively (Khasar et al., *Neuroscience* 1995, 67:189). However, its central actions are more powerful and result in analgesic effect.

Anilinoquinazolines: Derivatives of 4-anilinoquinazolines are widely described in the literature as powerful and selective inhibitors of the activity of tyrosine kinases from the family of EGF receptors (Fry et al., *Science* 1994, 265, 1093; Fry et al., *Pharmacol Ther.* 1999, 82, 207; and Levitzki et al., *Pharmacol. Ther.* 1999, 82, 231). Furthermore, knowledge of the inhibition process of these enzymes seems to be the way for the therapy of many diseases, like cancer, psoriasis, diabetes, cardiovascular diseases etc (Fry et al., *Science* 1994, 265, 1093). Based on this evidence, many detailed studies arose on the biological function of many derivatives from this structure class (Rewcastle et al., *J. Med. Chem.* 1995, 38, 3482; and Bridges et al., *J. Med. Chem.* 1996, 39, 267).

Many studies on the structure-activity relationship (SAR) involving many series of quinazoline derivatives lead to advances in power, specificity and pharmacokinetic properties of these inhibitors (Fry et al., *Pharmacol. Ther.* 1999, 82, 207; and Rewcastle et al., *Curr. Org. Chem.* 2000, 4, 679). Three quinazoline compounds are under clinical investigation in cancer patients: ZD1839 (Iressa) (Rewcastle et al., *Curr. Org. Chem.* 2000, 4, 679), CP358774 (Rewcastle et al., *Curr. Org. Chem.* 2000,4, 679; and Moyer et al., *Cancer Res.* 1997, 57, 4838) and CI1033 (Tsou et al., *J. Med. Chem.* 2001, 44, 2719). Pre-clinical data ($IC_{50}$ in the order of $pmol.L^{-1}$) support the possibility of using these compounds in conventional chemotherapy with potential anti-tumoral agents (Ciardiello et al., *Drugs* 2000, 60 (supl. 1), 25).

Inhibition power, in all series of evaluated and synthesized compounds, seems to be associated to electron donor substitute groups in positions 6 and/or 7 of quinazoline (OMe, OEt e $NH_2$), and to halogens (mainly Br and Cl), like substitutes in the meta position of the aniline ring. The meta-substituted aniline group showed to be the best substitute for position 4 of the quinazoline system (Bridges et al., *J. Med. Chem.* 1996, 39, 267).

Studies with quinazoline derivatives have not been limited only to the investigation of the activity of tyrosine kinase from the family of EGF receptor (Rewcastle et al., *Curr. Org.*

Chem. 2000, 4, 679). Prazosin is a quinazoline with antagonistic properties of α-adrenergic receptors. This compound has a vasodilator effect, and is used in the anti-hypertensive therapy, as well as some of its structural derivatives like ciclazosin, which has a stringer affinity to α1-adrenergic receptors, and may be applied in the treatment of benign prostate hyperplasia (Melchiorre et. al., *Bioorganic and Medicinal Chemistry Letters* 1998, 8, 1353-1358). Another good example is PD153035, which entered the stage of clinical triage by Sugen (like SU5271) for use in the treatment of skin diseases, like psoriasis and skin cancer (McMahon et al., WO9810767; *Chem. Abstr.* 1998, 128, 261949). Other examples of biologically active quinazolines are those presented as powerful and specific inhibitors of type 5 phosphodiesterase (PDE5) (Ukita et al., *J. Med. Chem.* 2001, 44, 2204). This enzyme is highly specific in the hydrolysis of the cyclic nucleotide cGMP (guanosine 3',5'-cyclic monophosphate), which controls vascular functions (Corbin et al., *J. Biol. Chem.* 1999, 274, 13729). Thus, an inhibitor that increases the cGMP level inside cells is considered a potential pharmaceutical for the treatment of cardiovascular diseases, such as hypertension, angina, and heart insufficiency (Ukita et al., *J. Med. Chem.* 2001, 44, 2204).

BRIEF SUMMARY OF THE IVENTION

The present invention relates to the use of anilinoquinazoline derivatives as adenosine kinase inhibitors. The 4-anilinoquinazoline compounds referred hereinafter have the molecular formula I, as shown in FIG. 1, wherein $R_1$ and $R_2$ are alkoxy group as methoxy (—$OCH_3$), and $R_3$ is hydrogen (—H), halogen (F, Cl, Br or I), methoxy (—$OCH_3$), methyl (—$CH_3$), acetyl [—$C(O)CH_3$], N,N-dimethylamino [—$N(CH_3)_2$] or nitro (—$NO_2$). The substituent $R_3$ may occupy positions 3' or 4' of the N-phenyl group, generating meta and para-substituted 4-anilinoquinazoline compounds.

The present invention also relates to the use 4-anilinoquinazoline derivatives as adenosine kinase inhibitors in the manufacture of a medicament for treating or preventing diseases which are benefited from the adenosine kinase inhibition.

The present invention also relates to the preferred compound 6,7-dimethoxy4-(3'-N',N'-dimethylaminoanilino) quinazoline, or a pharmaceutically acceptable salt thereof, particularly a hydrochloride salt.

BRIEF DESCRIPTION OF THE FIGURES

We refer to the following figures that accompany this descriptive report, in order to allow a better understanding and illustration of the present invention.

DETAILED DESCRIPTION OF THE INVENTION

Figure 1:
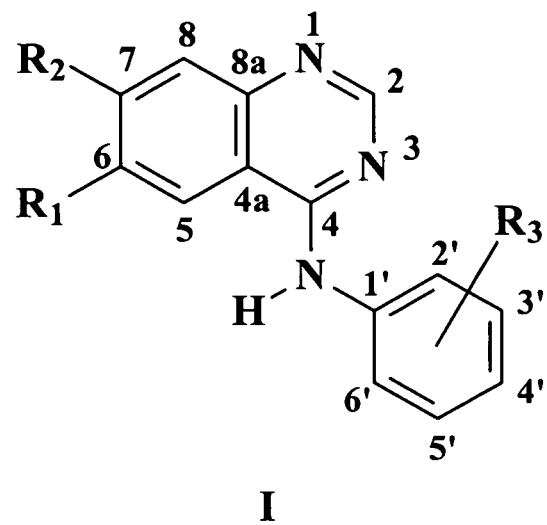
FIG. 1 presents Molecular Formula I, related to the 4-anilinoquinazoline derivatives, that is included in the scope of the present invention, wherein $R_1$ and $R_2$ are alkoxy group as methoxy (—$OCH_3$), and $R_3$ is hydrogen (—H), halogen (F, Cl, Br and I), methoxy (—$OCH_3$), methyl (—$CH_3$), acetyl [—$C(O)CH_3$], N,N-dimethylamino [—$N(CH_3)_2$] or nitro (—$NO_2$). The substituent $R_3$ may occupy positions 3' or 4' of group N-phenyl, generating meta and para-substituted 4-anilinoquinazoline compounds.
Figure 2:
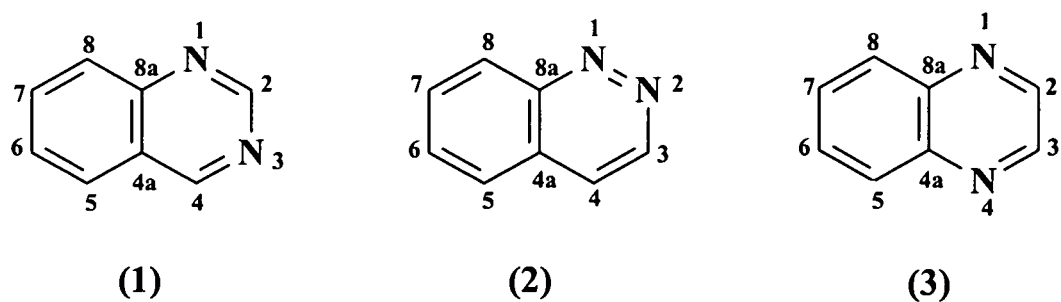
FIG. 2 presents different benzodiazine cores. Structure (1) represents a quinazoline, (2) represents a quinoline and (3) a quinoxaline. The name quinazoline (German: Chinazoline) was proposed, because these compounds are isomers of quinolines (2) and quinoxalines (3).

The present invention relates to the use of 4-anilinoquinazoline derivatives as adenosine kinase inhibitors having the Molecular Formula I (FIG. 1), wherein $R_1$ and $R_2$ are alkoxy group such as methoxy (—$OCH_3$), and $R_3$ is hydrogen (—H), halogen (F, Cl, Br and I), methoxy (—$OCH_3$), methyl (—$CH_3$), acetyl [—$C(O)CH_3$], N,N-dimethylamino [—$N(CH_3)_2$] and nitro (—$NO_2$) or a pharmaceutically acceptable salt thereof. The substituent $R_3$ may occupy positions 3' or 4' of the N-phenyl group, generating meta and para-substituted 4-anilinoquinazoline compounds.

The way of choosing 4-anilinoquinazoline substituents was established by structure-activity studies, in an attempt of allowing compounds with higher power and specificity to inhibit adenosine kinases. Thus, it was established that compounds of Formula I comprise all proper elements in a 4-anilinoquinazoline that possibly allow high power and/or efficiency for the inhibition of the enzyme. Such elements are electron donor substituents in positions 6 and 7 of the quinazoline, one small or medium-sized lipophilic substituent in positions meta orpara in the group N-phenyl (preferably in position meta), one free NH in position 4, and on free CH in positions 2, 5 and 8 of the quinazoline.

Therefore, the compounds included in the scope of the present invention are the following:

6,7-Dimethoxy-4-anilinoquinazoline
6,7-Dimethoxy-4-(3'-fluoroanilino)quinazoline
6,7-Dimethoxy-4-(4'-fluoroanilino)quinazoline
6,7-Dimethoxy-4-(3'-chloroanilino)quinazoline
6,7-Dimethoxy-4-(4'-chloroanilino)quinazoline
6,7-Dimethoxy-4-(3'-bromoanilino)quinazoline
6,7-Dimethoxy-4-(4'-bromoanilino)quinazoline
6,7-Dimethoxy-4-(3'-iodine)phenylaminequinazoline
6,7-Dimethoxy-4-(4'-iodoanilino)quinazoline
6,7-Dimethoxy-4-(3'-methoxyanilino)quinazoline
6,7-Dimethoxy-4-(4'-methoxyanilino)quinazoline
6,7-Dimethoxy-4-(3'-methylanilino)quinazoline
6,7-Dimethoxy-4-(4'-methylanilino)quinazoline
6,7-Dimethoxy-4-(3'-acetylanilino)quinazoline
6,7-Dimethoxy-4-(4'-acetylanilino)quinazoline
6,7-Dimethoxy-4-(3'-N',N'-dimethylaminoanilino)quinazoline
6,7-Dimethoxy-4-(4'-N',N'-dimethylaminoanilino)quinazoline
6,7-Dimethoxy-4-(3'-nitroanilino)quinazoline
6,7-Dimethoxy-4-(4'-nitroanilino)quinazoline or their pharmaceutically acceptable salts.

The more preferred compound of the present invention is 6,7-dimethoxy-4-(3'-N',N'-dimethylaminoanilino)quinazoline.

The following considerations upon the substituents of compounds of Formula I are important:

- the term "alkoxy" means an alkyl group attached to an oxygen atom. Representative examples of "alkoxy" groups comprise methoxy, ethoxy, terc-butoxy, propoxy and isobutoxy;
- the term "halogen" comprises fluorine, chlorine, bromine and iodine;
- the term "alkyl" means a straight or ramified chain of hydrocarbon. Representative examples of alkyl groups are methyl, ethyl, propyl, isopropyl, isobutyl, butyl, terc-butyl, sec-butyl, pentyl and hexyl;
- the term "acetyl" means a methyl attached to a carbonylic carbon atom;
- the term "N,N-dimethylamino" means two methyls attached to a nitrogen atom.

Compounds of the present invention may exist in forms that are non-solvated, as well as solvated, with pharmacologically acceptable solvents like water, DMSO, ethanol and similar. Generally, solvated forms are considered equivalent to non-solvated forms for the purposed of the present invention.

In the experimental stages, situations related to processing of the compounds are considered, which are described in Examples from 2 to 20, and the experimental conditions for obtaining them are the following:

(i) Solvents were evaporated in a rotating evaporator (Asten (250 rpm) and Wheaton (200 rpm)) after removing solid remains, such as drying agents, by filtering;

(ii) Melting points were determined in a MQAPF-301 equipment and are incorrect;

(iii) Structures of compounds of Formula I and its intermediates were characterized by their infrared spectra, mass and $^1$H RMN and by elementary analysis. Infrared spectra were obtained in a Perkin-Elmer FTIR-1600 or FTIR 1605 equipment. Yet mass spectra were obtained in a VG Auto-Spec (Varian) spectrometer. Data from the elementary analysis were obtained in Perkin-Elmer (2400) analyzer. $^1$H RMN spectra were acquired in an INOVA-500 (Varian) spectrometer, operating at 500 MHz. All $^1$H RMN spectra were obtained at 21° C. in $(CD_3)_2SO$, and referenced with $Me_4Si$. Values of $^1$H RMN signals were determined in delta ($\delta$) scale, and multiplicities are presented as following; d, dublet; dd, double dublet; ddd, double double dublets; t, triplet; dt, dublet of triplets; tdd, triplet of dublet of dublets.

Figure 3:
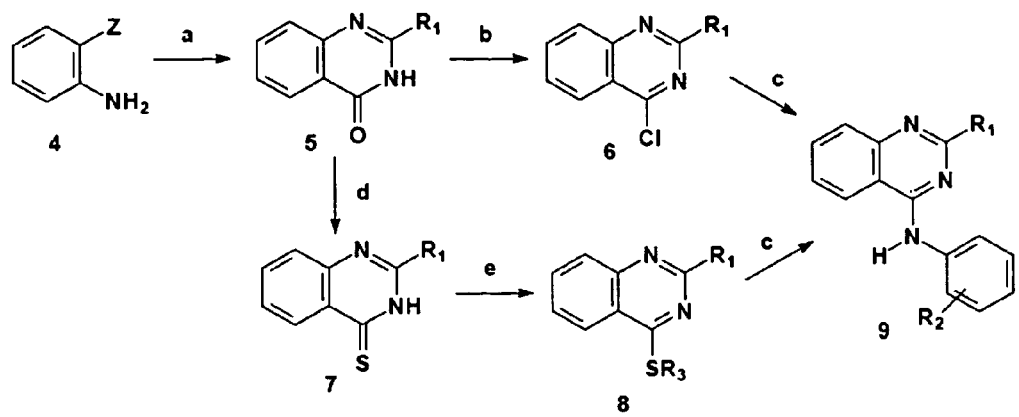
FIG. 3 presents Scheme 1, which presents stages for preparing 4-anilinoquinazolines (9) included in the present invention.
Figure 4:
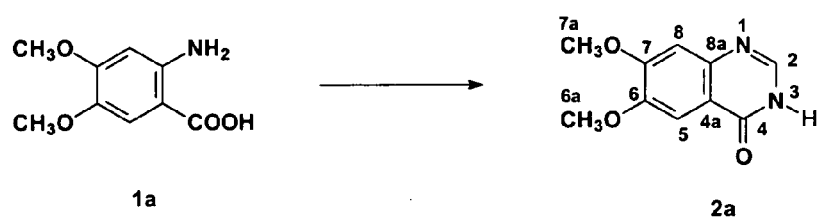
FIG. 4 presents experimental stages for preparing 6,7-dimethoxyquinazolin-4(3H)-one (2a), and experimental stages for preparing 4-chloro-6,7-dimethoxyquinazoline (3a).
Figure 4:
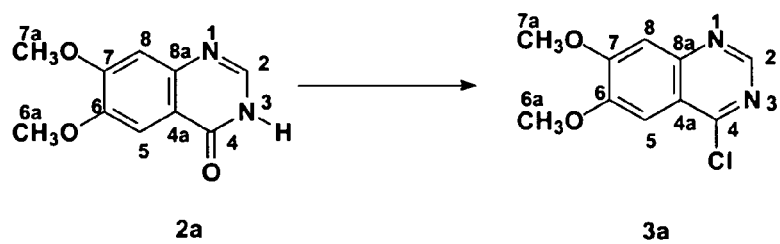
Figure 5:
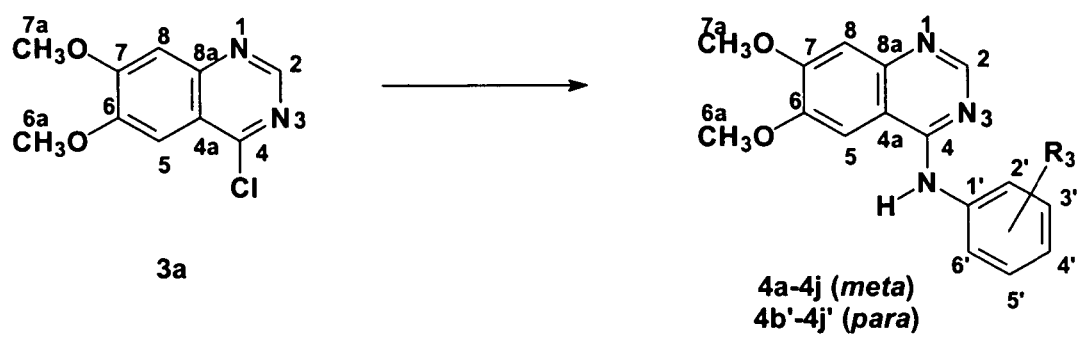
FIG. 5 presents the General Procedure for substituting chlorine, in 4-chloro-6,7-dimethoxyquinazoline (3a).

(v) The following abbreviations were used:
$(CD_3)_2SO$-deuteron dimethylsulfoxide
$Me_4Si$-tetramethylsilane
DMF-N,N-dimethylformamide
$CH_2Cl_2$-dichloromethane
$Na_2CO_3$-sodium carbonate
NaOH-sodium hydroxide A general review on quinazoline synthesis processes may be found in textbooks and in a recent thesis. Another review emphasizes that the most used start material has been anthranilic acid (4), according to the general method presented in Scheme 1, represented in FIG. 3.

In this procedure, the first step involves addition of a carbon unit to an anthranilic acid derivative (4), which leads to in situ cyclization to quinazoline (5) (Scheme 1). This transformation may be carried out using reagents like formic acid, formamide, and amidins. The synthesis of this precursor was described in 1895 by Niementowski, who reacted anthranilic acid with formamide. However, superior results are frequently obtained with reagents such as formamidine acetate. The second step in derivatization involves the conversion of intermediate 5 to 4-chloroquinazoline 6, through reaction with phosphoryl chloride ($POCl_3$) or with thionyl chloride, containing a catalytic amount of DMF. An alternative procedure, which is better for low soluble quinazolines, involves conversion to analog thione 7 followed by alkylation in sulfur, in order to provide an alkylthio derivative 8. Finally, the reaction of derivative 4-chloro (6) or of 4-alkylthio (8) with an aniline derivative provides the final product (9) (Scheme 1, FIG. 3).

In this way, synthetic stages explored for preparation of Formula I compounds (FIG. 1) and its intermediates are illustrated in Example 1. The synthetic method, which is already well described in the literature, and physic-chemical and spectroscopical data are described in Examples 1 to 20, as follows:

In Example 1, we describe experimental stages for preparation of 6,7-dimethoxyquinazolin-4(3H)-one (2) and 4-chloro-6,7-dimethoxyquinazoline (3a), which are precursors of 4-anilinoquinazoline derivatives from Formula I. Moreover, it presents the general substitution procedure of the chlorine atom of intermediate (3a), in order to synthesize all target-compounds described in Examples 2 to 20.

EXAMPLE 1

Obtainment of 6,7-dimethoxyquinazolin-4(3H)-one (2a)

A mixture of 2-amino-4,5-dimethoxybenzoic acid (1.0 g, 5.08 mmol) and formamidine acetate (4.50 g, 43.3 mmol) was disposed in a 50 mL ball. The solid mixture was heated at 140° C. in a silicone bath for eight hours. During heating, the fusion of solids happened, and then the resolidification of the reaction environment. The mixture was left cooling, and then a NaOH solution was added to it (0.33 mol.$L^{-1}$) until pH was adjusted to 8. The grayish pink solid was collected through filtering in a Büchner funnel, washed with water (3×10 mL), and dried in vacuum to provide the desired compound (0.79 g, 3.83 mmol, 76%), which was used without purification in the next stage: m.p. 296-298° C. (Lit. (Bridges et al., *J. Med. Chem.* 1996, 39, 267), m.p. 295-298° C.).

$^1$H RMN [500 MHz, (CD$_3$)$_2$SO, ppm] δ: 12.07 (1H, s, H-3), 8.00 (1H, s, H-2a), 7.45 (1H, s, H-5), 7.14 (1H, s, H-8), 3.91 (3H, s, H-6a), 3.87 (3H, s, H-7).

Obtainment of 4-chloro-6,7-dimethoxyquinazoline (3a)

A 6,7-dimethoxyquinazolin-4(3H)-one suspension (2a) (0.79 g, 3.83 mmol) in thionyl chloride (7.0 mL) containing 10 drops of N,N-dimethylformamide (DMF) was agitated and heated under reflux for three hours, until a solution was obtained. The reaction mixture was left cooling at room temperature. The reaction environment was diluted in dichloromethane and water (160 mL) and left in ice bath. The material was treated under agitation with 30 mL of saturated Na$_2$CO$_3$ solution. Na$_2$CO$_3$ was carefully added until pH was adjusted to 7-8 range. Then, the aqueous phase was extracted with CH$_2$Cl$_2$ (2×30 mL), and the organic phase compound was washed with salt solution (2×10 mL), dried over magnesium sulfate, filtered, and the solvent was evaporated in a rotatory evaporator in order to provide 6,7-dimethoxy-4-chloroquinazoline (3a) as a yellow solid (0.68 g, 3.03 mmol, 79%), which was used without purification in the next stage: melting point 185-187° C.

RMN of $^1$H [500 MHz, (CD$_3$)$_2$SO, ppm] δ: 8.90 (1H, s, H-2), 7.39 (1H, s, H-5), 7.34 (1H, s, H-8), 4.08 (6H, s, H-6a and H-7a).

IV (KBr/cm$^{-1}$) ν: 2975 (C—H), 1619 (C═N of an aromatic), 1511 (C═C of an aromatic), 1233 (C—O—C), 789 (C—H), 872 (C—Cl).

Obtainment of 6,7-Dimethoxy-4-[3'- or 4'-(R$_3$)-anilino]quinazoline (4a-4j and 4b'-4j'). With substituents R═H (a), F (b), Cl (c), Br (d), I (e), OCH$_3$ (f), CH$_3$ (g), C(O)CH$_3$ (h), N(CH$_3$)$_2$ (i) and NO$_2$ (j)

General chlorine substitution procedure: a mixture of 4-chloro-6,7-dimethoxyquinazoline (3a) (0.10 g, 0.445 mmol) and of the correspondent aniline (5.50 mmol) in isopropanol (20 mL) was mechanically agitated and heated to reflux temperature for two hours. We observed that when the heating of the reaction mixture reached the range of 70-90° C., the solid dissolved completely, and then began the precipitation of the desired compound, showing that the nucleophilic aromatic substitution reaction was happening. The yellow solids were filtered, washed with isopropanol (2×50 mL), and after vacuum drying, the desired compounds were obtained. Products were isolated as hydrochlorides through direct filtering of the reaction mixture.

According to this experimental procedure, the following compounds of Formula I (FIG. 1) were synthesized.

EXAMPLE 2

Obtainment of 6,7-Dimethoxy-4-(anilino)quinazoline hydrochloride (4a): Yield of 0.110 g (0.346 mmol, 77.0%), Melting Point 268-270° C. (Lit. (Bridges et al., *J. Med. Chem.* 1996, 39, 267) Melting Point>250° C.)

RMN of $^1$H [500 MHz, (CD$_3$)$_2$SO, ppm] δ: 11.46 (1H, s, NH), 8.80 (1H, s, H-2), 8.35 (1H, s, H-5), 7.70 (2H, d, $^3$J=8.0 Hz, H-2' e H-6'), 7.50 (2H, t, $^3$J=8.0 Hz, H-3' e H-5'), 7.38 (1H, s, H-8), 7.32 (1H, t, $^3$J=8,0 Hz, H-4'), 4.04 (3H, s, H-6a), 4.01 (3H, s, H-7a).

IV (KBr/cm$^{-1}$) ν: 3418 (N—H), 3062 (C—H of an aromatic), 1635-1459 (C═N of an aromatic), 1459 (C═C of an aromatic), 1279 (C—O—C), 867-748 (C—H).

MS(EI), m/z (%): 281.1 (M$^+$) (84.25), 280.1 (M–H)$^+$ (100).

Elementary analysis for C$_{16}$H$_{15}$N$_3$O$_2$.HCl (%)—calculated: C, 60.48; H, 5.07; N, 13.22. Determined: C, 60.48; H, 4.92; N, 13.16.

EXAMPLE 3

Obtainment of 6,7-Dimethoxy-4-(3'-fluoroanilino) quinazoline hydrochloride (4b): Yield of 0.100 g (0.298 mmol, 67%), Melting Point 219-221° C. (Lit. (Bridges et al., *J. Med. Chem.* 1996, 39, 267) Melting Point 253-254° C.)

RMN of $^1$H [500 MHz, (CD$_3$)$_2$SO, ppm] δ: 11.51 (1H, s, NH), 8.86 (1H, s, H-2), 8.41 (1H, s, H-5), 7.74 (1H, dt, $^3$J$_{H-F}$=11,0 Hz and $^4$J$_{H-H}$=2,2 Hz, H-2'), 7.63 (1H, ddd, $^3$J=8.3 Hz and $^4$J$_{meta}$=2.2 Hz, $^4$J$_{meta}$~1.0 Hz, H-6'), 7.52 (1H, dt, $^3$J$_{H-H}$=8.3 Hz and $^4$J$_{H-F}$=6.7 Hz, H-5'), 7.39 (1H, s, H-8), 7.15 (1H, tdd, $^3$J$_{H-H}$=$^3$J$_{H-F}$=8.3 Hz, $^4$J$_{H-H}$=2.2 Hz and $^4$J$_{H-H}$=2.2 Hz and $^4$J$_{H-H}$~1.0 Hz, H-4'), 4.04 (3H, s, H-6a), 4.00 (3H, s, H-7a).

IV (KBr/cm$^{-1}$) ν: 3412 (N—H), 3062 (C—H of an aromatic), 1635 (C═N of an aromatic), 1490 (C═C of an aromatic), 1279 (C—O—), 985 (C—F), 872-774 (C—H).

MS(EI), m/z (%): 299.0 (M$^+$) (91.4), 298.0 (M–H)$^+$ (100).

Elementary analysis for C$_{16}$H$_{14}$N$_3$O$_2$F.HCl (%)—calculated: C, 57.24; H, 4.50; N, 12.51. Determined: C, 57.14; H, 4.38; N, 12.34.

EXAMPLE 4

Obtainment of 6,7-Dimethoxy-4-(4'-fluoroanilino) quinazoline hydrochloride (4b'): Yield of 0.098 g (0.292 mmol, 65%), Melting Point 269-272° C. (Lit. (Barker, Patent EP 566226A1) Melting Point 227-230° C.)

RMN of $^1$H [500 MHz, (CD$_3$)$_2$SO, ppm] δ: 11.56 (1H, s, NH), 8.79 (1H, s, H-2), 8.40 (1H, s, H-5), 7.75 (2H, dd, $^3$J=9.0 Hz and $^4$J$_{H-F}$=5.0 Hz, H-2' e H-6'), 7.38 (1H, s, H-8), 7.32 (2H, t, $^3$j=9.0 Hz, H-3' e H-5'), 4.02 (3H, s, H-6a), 3.98 (3H, s, H-7a).

IV (KBr/cm$^{-1}$) ν: 3418 (N—H), 3031 (C—H of an aromatic), 1635 (C═N of an aromatic), 1511 (C═N of an aromatic), 1284 (C—O—C), 826 (C—F), 774 (C—H).

MS(EI), m/z (%): 299.1 (M$^+$) (92), 298.1 (M–H)$^+$ (100).

Elementary analysis for C$_{16}$H$_{14}$N$_3$O$_2$F.HCl (%)—calculated: C, 57.24; H, 4.50; N, 12.51. Determined: C, 57.22; H, 4.41; N, 12.38.

EXAMPLE 5

Obtainment of 6,7-Dimethoxy-4-(3'-chloroanilino) quinazoline hydrochloride (4c): yield of 0.113 g (0.321 mmol, 72%), Melting Point 226-228° C. (Lit. (Bridges et al., *J. Med. Chem.* 1996, 39, 267), Melting Point 261-262° C.)

RMN of $^1$H [500 MHz, (CD$_3$)$_2$SO, ppm] δ: 11.60 (1H, s, NH), 8.88 (1H, s, H-2), 8.45 (1H, s, H-5), 7.93 (1H, t, $^3$J=2.0 Hz, H-2'), 7.77 (1H, ddd, $^3$J=8.0 Hz, $^4$J=2.0 Hz and $^4$J~1.0 Hz, H-4'), 7.51 (1H, t, $^3$J=8.0 Hz, H-5'), 7.40 (1H, s, H-8), 7.37

(1H, ddd, $^3J$=8.0 Hz, $^4J$=2.0 Hz and $^4J$~1.0 Hz, H-6'), 4.04 (3H, s, H-6a), 4.00 (3H, s, H-7a).

IV (KBr/cm$^{-1}$) ν: 3428 (N—H), 3041 (C—H of an aromatic), 1640 (C—N of an aromatic), 1521 (C—C of an aromatic), 1284 (C—O—C), 991 (C—Cl), 877-774 (C—H).

MS(EI), m/z (%): 315.0 (M$^+$) (71.3), 314.0 (M–H)$^+$ (100).

Elementary analysis for $C_{16}H_{14}N_3O_2Cl.HCl$ (%)—calculated: C, 54.56; H, 4.29; N, 11.93. Determined: C, 54.43; H, 4.17; N, 11.27.

EXAMPLE 6

Obtainment of 6,7-Dimethoxy-4-(4'-chloroanilino) quinazoline hydrochloride (4c') (Hennequin et al., *J. Med. Chem.* 1999, 42, 5369): Yield of 0.105 g (0.298 mmol, 67%), Melting Point 282-284° C.

RMN of $^1$H [500 MHz, $(CD_3)_2SO$, ppm] δ: 11.16 (1H, s, NH); 8.74 (1H, s, H-2); 8.28 (1H, s, H-5), 7.79 (2H, d, $^3J$=8.5 Hz, H-2' and H-6'), 7.50 (2H, d, $^3J$=8.5 Hz, H-3' and H-5'), 7.33 (1H, s, H-8), 4.00 (3H, s, H-6a); 3.97 (3H, s, H-7a).

IV (KBr/cm$^{-1}$) ν: 3397 (N—H), 3041 (C—H of an aromatic), 1635 (C—N of an aromatic), 1516 (C—C of an aromatic), 1243 (C—O—C), 985 (C—Cl), 857-774 (C—H).

MS(EI), m/z (%): 315.0 (M$^+$) (82.8), 314.0 (M–H)$^+$ (100).

Elementary analysis for $C_{16}H_{14}N_3O_2Cl.HCl$ (%)—calculated: C, 54.56; H, 4.29; N, 11.93. Determined: C, 54.77; H, 4.49; N, 11.27.

EXAMPLE 7

Obtainment of 6,7-Dimethoxy-4-(3'-bromoanilino) quinazoline hydrochloride (4d): Yield of 0.165 g (0.416 mmol, 93%), Melting Point 263-265° C (Lit. (Bridges et al., *J. Med. Chem.* 1996, 39, 267), Melting Point 264-266° C.)

RMN of $^1$H [500 MHz, $(CD_3)_2SO$, ppm] δ: 11.70 (1H, s, NH), 8.88 (1H, s, H-2), 8.45 (1H, s H-5), 8.04 (1H, t, $^4J$=2.0 Hz, H-2'), 7.80 (1H, ddd, $^3j$=8.0 Hz and $^4J$~1.0 Hz, H4'), 7.49 (1H, ddd, $^3J$=8.0 Hz, $^4J$=2.0 Hz and $^4J$~1.0 Hz, H-6'), 7.43 (1H, t, $^3J$=8.0 Hz, H-5'), 7.39 (1H, s, H-8), 4.03 (3H, s, H-6a), 4.00 (3H, s, H-7a).

IV (KBr/cm$^{-1}$) ν: 3418 (N—H), 3031 (C—H of an aromatic), 1640 (C—N of an aromatic), 1521 (C—C of an aromatic), 1279 (C—O—C), 872-779 (C—H), 600 (C—Br).

MS(EI), m/z (%): 359.0 (M$^+$) (77.5), 360.0 (M–H)$^+$ (100).

Elementary analysis for $C_{16}H_{14}N_3O_2Br.HCl$ (%)—calculated: C, 48.45; H, 3.81; N, 10.59. Determined: C, 48.85; H, 3.54; N, 10.64.

EXAMPLE 8

Obtainment of 6,7-Dimethoxy-4-(4'-bromoanilino) quinazoline hydrochloride (4d'): Yield of 0.126 g (0.318 mmol, 71%), Melting Point 277-279° C.

RMN of $^1$H [500 MHz, $(CD_3)_2SO$, ppm] δ: 11.19 (1H, s, NH), 8.88 (1H, s, H-2), 8.22 (1H, s, H-5), 7.70 (4H, high singlet, H-2', H-3', H-5' and H-6'), 7.32 (1H, s, H-8), 4.04 (3H, s, H-6a), 4.02 (3H, s, H-7a).

IV (KBr/cm$^{-1}$) ν: 3449 (N—H), 3144 (C—H of an aromatic), 1629 (C—N of an aromatic), 1516 (C—C of an aromatic), 1284 (C—O—C), 867-774 (C—H), 501 (C—Br).

MS(EI), m/z (%): 358.9 (M$^+$) (81.1), 358.9 (M–H)$^+$ (100).

Elementary analysis for $C_{16}H_{14}N_3O_2Br.HCl$ (%)—calculated: C, 48.45; H, 3.81; N, 10.59. Determined: C, 48.38; H, 3.61; N, 10.54.

EXAMPLE 9

Obtainment of 6,7-Dimethoxy-4-(3'-iodoanilino) quinazoline hydrochloride (4e): Yield of 0.119 g (0.268 mmol, 60%), Melting Point 218-220° C. (Lit. (Bridges et al., *J. Med. Chem.* 1996, 39, 267), Melting Point 273° C.)

RMN of $^1$H [500 MHz, $(CD_3)_2SO$, ppm] δ: 11.50 (1H, s, NH), 8.85 (1H, s, H-2), 8.39 (1H, s H-5), 8.15 (1H, t, $^4J$=1.5 Hz, H-2'), 7.81 (1H, ddd, $^3J$=8.0 Hz, $^4J$=1.5 Hz and $^4J$~1.0 Hz, H-4'), 7.70 (1H, ddd, $^3J$=8.0 Hz, $^4J$=1.5 Hz and $^4J$~1.0 Hz, H-6'), 7.39 (1H, s, H-8), 7.27 (1H, t, $^3J$=8.0 Hz, H-5'), 4.03 (3H, s, H-6a), 4.00 (3H, s, H-7a).

IV (KBr/cm$^{-1}$) ν: 3418 (N—H), 3026 (C—H of an aromatic), 1629 (C—N of an aromatic), 1516 (C—C of an aromatic), 1279 (C—O—C), 877-779 (C—H), 600 (C—I).

MS(EI), m/z (%): 406.9 (M$^+$) (95), 405.9 (M–H)$^+$ (100).

Elementary analysis for $C_{16}H_{14}N_3O_2I.HCl$ (%)—calculated: C, 43.31; H, 3.41; N, 9.47. Determined: C, 43.26; H, 3.35; N, 9.26.

EXAMPLE 10

Obtainment of 6,7-Dimethoxy-4-(4'-iodoanilino) quinazoline hydrochloride (4e'): Yield of 0.121 g (0.273 mmol, 61%), Melting Point 266-269° C.

RMN of $^1$H [500 MHz, $(CD_3)_2SO$, ppm] δ: 11.50 (1H, s, NH), 8.83 (1H, s, H-2), 8.38 (1H, s, H-5), 7.82 (2H, d, $^3J$=8,5 Hz, H-3' and H-5'), 7.58 (2H, d, $^3J$=8.5 Hz, H-2' and H-6'), 7.37 (1H, s, H-8), 4.02 (3H, s, H-6a), 4.00 (3H, s, H-7a).

IV (KBr/cm$^{-1}$) ν: 3397 (N—H), 3031 (C—H of an aromatic), 1635 (C—N of an aromatic), 1516 (C—C of an aromatic), 1290 (C—O—C), 872-779 (C—H), 501 (C—I).

MS(EI), m/z (%): 407.0 (M$^+$) (100), 406.0 (M–H)$^+$ (93.2).

Elementary analysis for $C_{16}H_{14}N_3O_2I.HCl$ (%)—calculated: C, 43.31; H, 3.41; N, 9.47. Determined: C, 43.44; H, 3.42; N, 9.28.

EXAMPLE 11

Obtainment of 6,7-Dimethoxy-4-(3'-methoxyanilino) quinazoline hydrochloride (4f): Yield of 0.094 g (0.270 mmol, 61%), Melting Point 216-218° C.

RMN of $^1$H [500 MHz, $(CD_3)_2SO$, ppm] δ: 11.39 (1H, s, NH), 8.81 (1H, s, H-2), 8.37 (1H, s, H-5), 7.39 (1H, s, H-8), 7.39 (1H, t, $^3J$=8.0 Hz; H-5'), 7.35 (1H, t, $^4J$=2.0 Hz, H-2'), 7.31 (1H, ddd, $^3J$=8.0 Hz, $^4J$=2.0 Hz e $^4J$~1.0 Hz, H-6'), 6.90 (1H, ddd, $^3J$=8.0 Hz, $^4J$=2.5 Hz and $^4J$~1.0 Hz, H-4'), 4.03 (3H, s, H-6a), 4.00 (3H, s, H-7a), 3.80 (3H, s, H-7').

IV (KBr/cm$^{-1}$) ν: 3438 (N—H), 3005 (C—H of an aromatic), 1635 (C—N of an aromatic), 1496 (C—C of an aromatic), 1279 (C—O—C), 872-774 (C—H).

MS(EI), m/z (%): 311.0 (M$^+$) (79.3), 310.0 (M–H)$^+$ (100).

Elementary analysis for $C_{17}H_{17}N_3O_3.HCl$ (%)—calculated: C, 58.71; H, 5.22; N, 12.08. Determined: C, 58.52; H, 5.00; N, 12.17.

EXAMPLE 12

Obtainment of 6,7-Dimethoxy-4-(4'-methoxyanilino) quinazoline hydrochloride (4f): Yield of 0.101 g (0.291 mmol, 65%), Melting Point 205-207° C.

RMN of $^1$H [500 MHz, $(CD_3)_2SO$, ppm] δ: 11.52 (1H, s, NH), 8.76 (1H, s, H-2), 8.38 (1H, s, H-5), 7.59 (2H, d, $^3J$=9.0 Hz; H-2' and H-6'), 7.38 (1H, s, H-8), 7.02 (2H, d, $^3J$=9.0 Hz, H-3'and H-5'), 4.01 (3H, s, H-6a), 3.97 (3H, s, H-7a), 3.80 (3H, s, H-7').

IV (KBr/cm$^{-1}$) ν: 3403 (N—H), 2949 (C—H of an aromatic), 1635 (C—N of an aromatic), 1516 (C—C of an aromatic), 1243 (C—O—C), 862-774 (C—H).

MS(EI), m/z (%): 311.1 (M$^+$) (100), 310.1 (M–H)$^+$ (64.9).

Elementary analysis for $C_{17}H_{17}N_3O_3$.HCl (%)—calculated: C, 58.71; H, 5.22; N, 12.08. Determined: C, 58.68; H, 5.03; N, 12.10.

EXAMPLE 13

Obtainment of 6,7-Dimethoxy-4-(3'-methylanilino) quinazoline hydrochloride (4g) (Fry et al., *Annu. Rep. Med. Chem.* 1996, 31, 151): Yield of 0.075 g (0.226 mmol, 51%), Melting Point 221-223° C.

RMN of $^1$H [500 MHz, $(CD_3)_2SO$, ppm] δ: 11.24 (1H, s, NH), 8.78 (1H, s, H-2), 8.29 (1H, s, H-5), 7.50 (2H, signal overlap, H-2' and H-5'), 7.36 (2H, signal overlap, H-8 and H-6'), 7.14 (1H, d, $^3J$=8.0 Hz, H4'), 4.02 (3H, s, H-6a), 3.99 (3H, s, H-7a), 2.37 (3H, s, H-7'), IV (KBr/cm$^{-1}$) ν: 3418 (N—H), 3008 (C—H of an aromatic), 1635 (C—N of an aromatic), 1511 (C—C of an aromatic), 1279 (C—O—C), 775 (C—H).

MS(EI), m/z (%): 295.0 (M$^+$) (87.4), 294.0 (M–H)$^+$ (100).

Elementary analysis for $C_{17}H_{17}N_3O_2$.HCl (%)—calculated: C, 61.54; H, 5.47; N, 12.66. Determined: C, 61.96; H, 5.55; N, 12.96.

EXAMPLE 14

Obtainment of 6,7-Dimethoxy-4-(4'-methylanilino) quinazoline hydrochloride (4g'): Yield of 0.096 g (0.290 mmol, 65%), Melting Point 227-229° C.

RMN of $^1$H [500 MHz, $(CD_3)_2SO$, ppm] δ: 11.26 (1H, s, NH), 8.75 (1H, s, H-2), 8.30 (1H, s, H-5), 7.57 (2H, d, $^3J$=8.3 Hz, H-2' and H-6'), 7.36 (1H, s, H-8), 7.28 (2H, d, $^3J$=8.3 Hz, H-3' and H-5'), 4.01 (3H, s, H-6a), 3.98 (3H, s, H-7a), 2.35 (3H, s, H-7').

IV (KBr/cm$^{-1}$) ν: 3419 (N—H), 2949 (C—H), 1635 (C—N of an aromatic), 1506 (C—C of an aromatic), 1279 (C—O—C), 867-779 (C—H).

MS(EI), m/z (%): 295.1 (M$^+$) (85.1), 294.1 (M–H)$^+$ (100).

Elementary analysis for $C_{17}H_{17}N_3O_2$.HCl (%)—calculated: C, 61.54; H, 5.47; N, 12.66. Determined: C, 61.27; H, 5.53; N, 12.42.

EXAMPLE 15

Obtainment of 6,7-Dimethoxy-4-(3'-acetylanilino) quinazoline hydrochloride (4h): Yield of 0.097 g (0.270 mmol, 61%), Melting Point 219-221° C (Lit. (Barker, Patent No. 566226A1) Melting Point>240° C.)

RMN of $^1$H [500 MHz, $(CD_3)_2SO$, ppm] δ: 11.49 (1H, s, NH), 8.79 (1H, s, H-2), 8.45 (1H, s, H-5), 8.34 (1H, t, $^4J$=2.0 Hz, H-2'), 8.10 (1H, ddd, $^3J$=8.1 Hz, $^4J$=2.1 Hz, $^4J$=1.1 Hz, H-6'), 7.87 (1H, ddd, $^3J$=8.0 Hz, $^4J$=1.7 Hz, $^4J$=1.1 Hz, H-4'), 7.62 (1H, t, $^3J$=8.0 Hz, H-5'), 7.42 (1H, s, H-8), 4.05 (3H, s, H-6a), 3.99 (3H, s, H-7a), 2.63 (3H, s, H-8').

IV (KBr/cm$^{-1}$) ν: 3428 (N—H), 3036 (C—H of an aromatic), 1681 (C=O), 1635 (C—N of an aromatic), 1516 (C—C of an aromatic), 1279 (C—O—C), 882-779 (C—H).

MS(EI), m/z (%): 323.0 (M$^+$) (83.9), 322.0 (M–H)$^+$ (100).

Elementary analysis for $C_{18}H_{17}N_3O_3$.HCl (%)—calculated: C, 60.09; H, 5.04; N, 11.68. Determined: C, 59.07; H, 4.69; N, 11.72.

EXAMPLE 16

Obtainment of 6,7-Dimethoxy-4-(4'-acetylanilino) quinazoline hydrochloride (4h'): Yield of 0.110 g (0.306 mmol, 69%), Melting Point 218-220° C.

RMN of $^1$H [500 MHz, $(CD_3)_2SO$, ppm] δ: 11.33 (1H, s, NH), 8.84 (1H, s, H-2), 8.35 (1H, s, H-5), 8.03 (2H, d, $^3J$=9.0 Hz, H-3' and H-5'), 7.98 (2H, d, $^3J$=9.0 Hz, H-2' and H-6'), 7.36 (1H, s, H-8), 4.03 (3H, s, H-6a), 3.98 (3H, s, H-7a), 2.60 (3H, s, H-8').

IV (KBr/cm$^{-1}$) ν: 3412 (N—H), 2995 (C—H of an aromatic), 1671 (C=O), 1635 (C—N of an aromatic), 1516 (C—C of an aromatic), 1279 C—O—C, 872-779 (C—H).

MS(EI), m/z (%): 323.1 (M$^+$) (73), 322.1 (M–H)$^+$ (100).

Elementary analysis for $C_{18}H_{17}N_3O_3$.HCl (%)—calculated: C, 60.09; H, 5.04; N, 11.68. Determined: C, 59.07; H, 4.67; N, 11.73.

EXAMPLE 17

Obtainment of 6,7-Dimethoxy-4-(3'-N',N'-dimethylaminoanilino)quinazoline hydrochloride (4i): Yield of 0.128 g (0.355 mmol; 80%), Melting Point 198-200° C.

RMN of $^1$H [500 MHz, $(CD_3)_2SO$, ppm] δ: 10.39 (1H, s, NH), 8.60 (1H, s, H-2), 8.11 (1H, s, H-5), 7.27 (1H, s, H-8), 7.22 (1H, t, $^3J$=8.0 Hz, H-5'), 7.10 (2H, overlap of H-2' and H-6'), 6.59 (1H, ddd, $^3J$=8.2 Hz, $^4J$=2.4 Hz and $^4J$~1.0 Hz, H-4'), 3.99 (3H, s, H-6a), 3.95 (3H, s, H-7a), 2.93 (6H, s, H-7' and H-8').

IV (KBr/cm$^{-1}$) ν: 3418 (N—H), 3119 (C—H of an aromatic), 1624 (C—N of an aromatic), 1511 (C—C of an aromatic), 1228 C—O—C, 846-764 (δ=C—H).

MS(EI), m/z (%): 324.1 (M$^+$) (100), 323.1 (M–H)$^+$ (75.5).

Elementary analysis for $C_{18}H_{20}N_4O_2$.HCl (%)—calculated: C, 59.91; H, 5.87; N, 15.53. Determined: C, 60.01; H, 5.66; N, 15.62.

EXAMPLE 18

Obtainment of 6,7-Dimethoxy-4-(4'-N',N'-dimethylaminoanilino)quinazoline hydrochloride (4i'): Yield of 0.110 g (0.305 mmol, 69%), Melting Point 204-206° C.

RMN of $^1$H [500 MHz, $(CD_3)_2SO$, ppm] δ: 11.83 (1H, s, NH), 8.80 (1H, s, H-2), 8.51 (1H, s, H-5), 7.80 (2H, d, $^3J$=8.50 Hz, H-2' and H-6'), 7.59 (2H, d, $^3J$=8.50 Hz, H-3' and H-5'), 7.42 (1H, s, H-8), 4.03 (3H, s, H-6a), 3.98 (3H, s, H-7a), 3.11 (6H, s, H-7').

MS(EI), m/z (%): 324.1 (M$^+$) (100), 323.1 (M–H)$^+$ (23.2).

Elementary analysis for $C_{18}H_{20}N_4O_2$.HCl (%)—calculated: C, 59.91; H, 5.87; N, 15.53. Determined: C, 59.34; H, 5.60; N, 15.29.

EXAMPLE 19

Obtainment of 6,7-Dimethoxy-4-(3'-nitroanilino) quinazoline hydrochloride (4j): Yield of 0.093 g (0.256 mmol, 58%), Melting Point 279-281° C. (Lit. (Barker, Patent No. 566226A1) Melting Point>240° C.)

RMN of $^1$H [500 MHz, $(CD_3)_2SO$, ppm] δ: 11.10 (1H, s, NH), 8.82 (1H, s H-2), 8.76 (1H, t, $^4J$=2.0 Hz, H-2'), 8.34 (1H, s, H-5), 8.33 (1H, ddd, $^3J$=8.0 Hz, $^4J$=2.2 Hz, $^4J$~1.0 Hz, H-4'), 8.07 (1H, ddd, $^3J$=8.2 Hz, $^4J$=2.2 Hz and $^4J$~1.0 Hz, H-6'), 7.74 (1H, t, $^3J$=8.5 Hz, H-5'), 7.31 (1H, s, H-8), 4.04 (3H, s, H-6a), 4.00 (3H, s, H-7a).

IV (KBr/cm$^{-1}$) v: 3443 (N—H), 3026 (C—H of an aromatic), 1635 (C—N of an aromatic), 1511 (C—C of an aromatic), 1532 ($NO_2$), 1284 C—O—C, 872-733 (C—H).

MS(EI), m/z (%): 326.0 (M$^+$) (100), 325.0 (M–H)$^+$ (83.5).

Elementary analysis for $C_{16}H_{14}N_4O_4$·HCl (%)—calculated: C, 52.97; H, 4.17; N, 15.44. Determined: C, 52.68; H, 4.04; N, 15.04.

EXAMPLE 20

Obtainment of 6,7-Dimethoxy-4-(4'-nitroanilino) quinazoline hydrochloride (4j'): Yield of 0.121 g (0.334 mmol, 75%), Melting Point 228-230° C.

RMN of $^1$H [500 MHz, $(CD_3)_2SO$, ppm] δ: 10.70 (1H, s, NH), 8.78 (1H, s, H-2), 8.32 (2H, d, $^3J$=9.0 Hz, H-3' and H-5'), 8.18 (2H, d, $^3J$=9.0 Hz, H-2' and H-6'), 8.11 (1H, s, H-5), 7.31 (1H, s, H-8), 4.02 (3H, s, H-6a), 4.00 (3H, s, H-7a).

IV (KBr/cm$^{-1}$) v: 3428 (N—H), 3119 (C—H of an aromatic), 1635 (C—N of an aromatic), 1511 (C—C of an aromatic), 1573 ($NO_2$), 1279 C—O—C, 867-779 (C—H).

MS(EI), m/z (%): 326.1 (M$^+$) (86.9), 325.1 (M–H)$^+$ (100).

Elementary analysis for $C_{16}H_{14}N_4O_4$·HCl (%)—calculated: C, 52.97; H, 4.17; N, 15.44. Determined: C, 52.76; H, 4.10; N, 14.98.

EXAMPLE 21

Biological Methods

Pharmacological Action Mechanisms

We present results from experiments that support the present claim.

I. Effect on Adenosine Bioavailability and on Cardiac Adenosine Kinase Activity.

Figure 6:
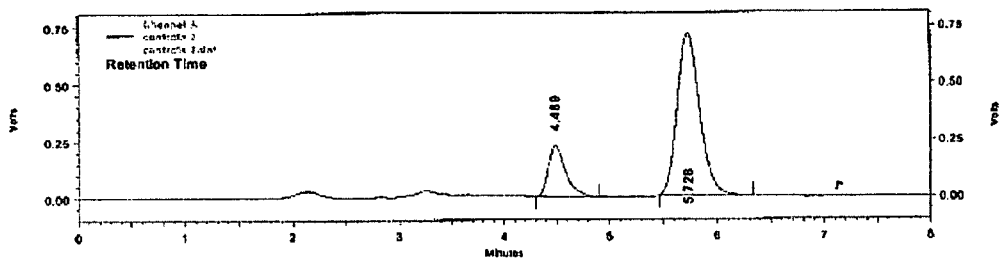
FIG. 6 presents Chromatograms obtained through HPLC experiments of rat myocardium extracts for dosage of tissue adenosine and AMP.
Figure 6:
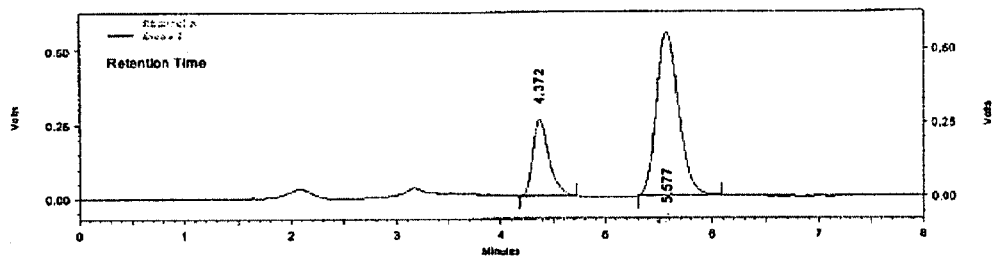

Physiological and pharmacological data of experiments carried out with quinazoline compounds point out that their cardiovascular effects are mediated by adenosine or by the activation of its receptors. We conducted adenosine dosages in the myocardium of isolated rat hearts with compounds 4d (Example 7) and 4i (Example 17). Chromatograms obtained through HPLC experiments in rat myocardium extracts for dosage of tissue adenosine and AMP are presented in FIG. 6. As pointed out in the chromatograms ($1^{st}$ peak=adenosine; $2^{nd}$ peak=AMP), the treatment with the compound 4d increased substantially the amount of myocardial adenosine. Average results point out a basal adenosine value of 0.48 nmol/mg of protein, and in hearts treated with 4d values were 0.75 nmol/mg of protein.

Experiments conducted in HPLC with adenosine derivatized using 2-chloroacetaldehyde for fluorescence detection used as a substrate in myocardium extracts, were able to confirm our hypothesis that compounds 4d (Example 7) and 4i (Example 17) are adenosine kinase inhibitors.

II. Effect of Quinazoline Compounds on Systolic Pressure of the Left Ventricle and Heart Rate of Isolated Rat Hearts.

Figure 7:
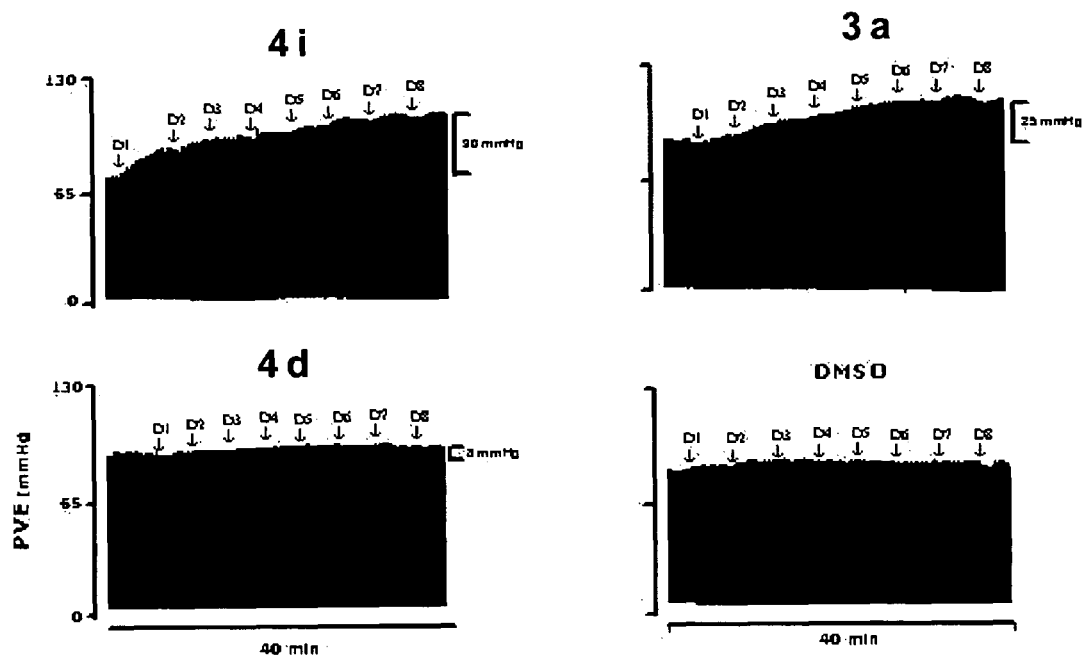
FIG. 7 shows representative Examples of systolic pressure records of the left ventricle (LVP) from concentration-response experiments of quinazoline compounds in isolated rat hearts.

Next, typical examples of pressure records are represented, which were conducted to evaluate the effect of injections of increased concentrations of quinazoline compounds, as well as the vehicle (DMSO), on the function of isolated rat hearts. We evaluated the effects of three different quinazoline compounds (4d (Example 7), 3a (Example I) and 4i (Example 17)). All compounds caused increase in the systolic pressure of the left ventricle (LVP), depending on the injected concentration, an effect that was not observed when the vehicle DMSO was separately administered. As demonstrated in the following examples, the compounds tested presented different potencies of their pressor effects in isolated hearts. 4i (Example 17) was the compound that produced a higher pressor response, when infused in concentrations between 30 pM-2 μM (maximum pressor response=27±3 mmHg), while 4d (Example 7) presented the lowest response (maximum pressor response=8±4 mmHg). Representative examples of systolic pressure records of the left ventricle (LVP) from concentration-response experiments with quinazoline compounds in isolated rat hearts are presented in FIG. 7.

Figure 8:
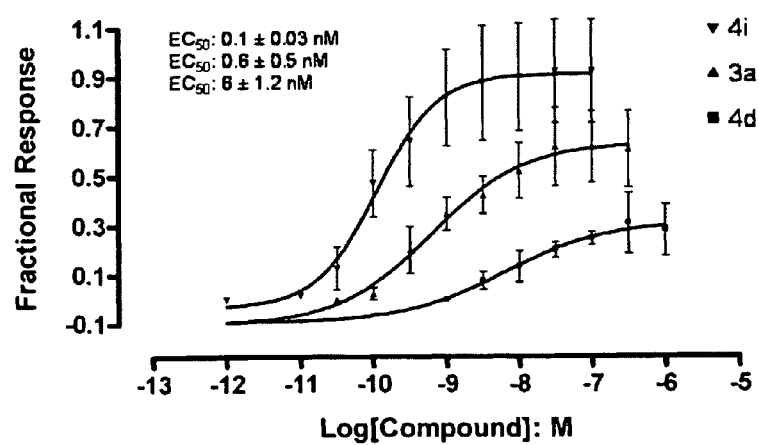
FIG. 8 presents concentration-response curves for compounds 4d (Example 7), 3a (Example 1) and 4i (Example 17) on the systolic pressure of the left ventricle in isolated rat hearts (expressed as fractional values).

Next, we present concentration-response relationships of arterial pressure and heart frequency, respectively, of the three quinazoline compounds mentioned before. Systolic pressure responses of the left ventricle were expressed as fractional values, while heart rate responses were expressed as absolute values. In Table 1, we present values of $E_{max}$, $EC_{50}$ (nM) and $LogEC_{50}$ in the fractional pressor response to infusion of increased concentrations of compounds like 4d (Example 7), 3a (Example 1) and 4i (Example 17) in isolated rat hearts (mean±S.E.M.). In FIG. 8, we present concentration-response curves to compounds 4d (Example 7), 3a (Example 1) and 4i (Example 17) on systolic pressure of the left ventricle in isolated rat hearts (expressed as fractional values). Data are presented as mean±S.E.M. *p<0.05 compared to response to 4i (Example 17). $EC_{50}$: concentration of the drug that produces half of the maximum effect.

TABLE 1

|  | 4i (Example 17) | 3a (Example 1) | 4d (Example 7) |
| --- | --- | --- | --- |
| $E_{max}$ | 0.9 ± 0.2 | 0.6 ± 0.2 | 0.3 ± 0.1 |
| $EC_{50}$ | 0.1 ± 0.03 | 0.6 ± 0.5 | 6.0 ± 1.2 |
| $LogEC_{50}$ | −9.9 ± 0.3 | −9.2 ± 0.5 | −8.2 ± 0.2 |

The increase in systolic pressure was approximately 35%, 30% and 14% for 4i (Example 17), 3a (Example 1) and 4d (Example 7), respectively, according to basal absolute values of systolic pressure. $E_{max}$ values calculated for the respective curves were 0.9±0.2 (4i, Example 17); 0.6±0.2 (3a, Example 1); 0.3±0.1 (4d, Example 7), in fractional values (Table 1), but the statistical test did not demonstrate significant difference between groups. $EC_{50}$ values for pressure curves of 4i (Example 17) and of 3a (Example 1) were statistically higher than those of 4d (Example 7). However, there was no difference between $EC_{50}$ of 4i (Example 17) and 3a (Example 1). Responding to the three compounds mentioned, there a decrease in the heart rate dependent concentration. The bradycardia responses were different from each other, and were approximately 24%, 29% and 25% for 4i (Example 17), 3a (Example 1) and 4d (Example 7), respectively, if compared to basal values. In Table 2, we present initial and final values of heart rate (bpm), responding to infusions of increased concentrations of 4i (Example 17), 3a (Example 1) and 4d (Example 7) in isolated rat hearts (mean±S.E.M).

TABLE 2

|  | 4i (Example 17) | 3a (Example 1) | 4d (Example 7) |
|---|---|---|---|
| Initial heart rate | 228 ± 7 | 242 ± 5 | 219 ± 12 |
| Final heart rate | 173 ± 8 | 173 ± 1 | 164 ± 3 |

Figure 9:
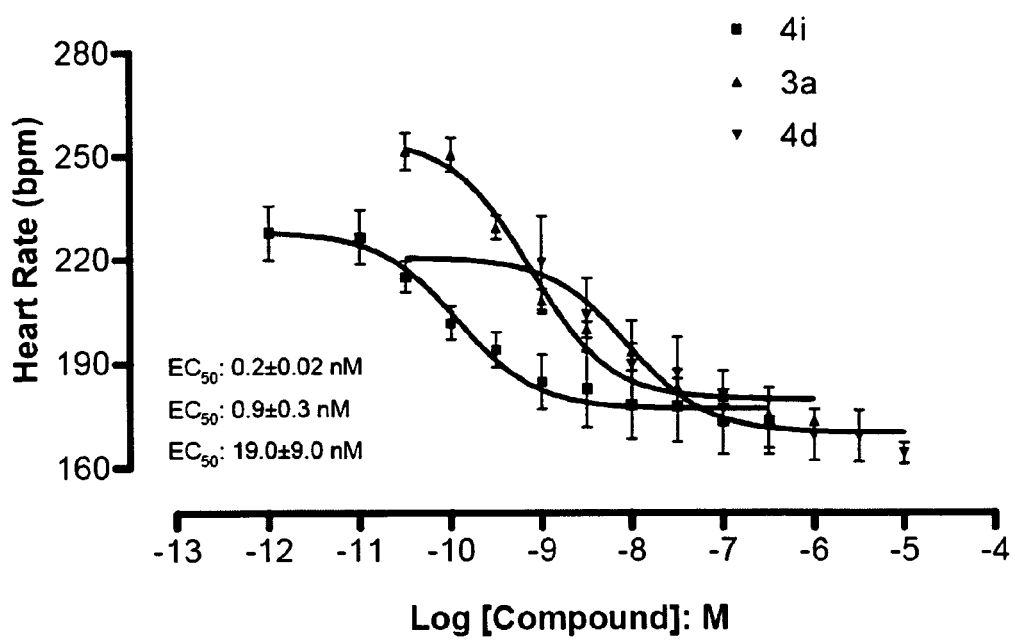
FIG. 9 presents concentration-response curves for 4i (Example 17), 3a (Example 1) and 4d (Example 7) on the heart rate of isolated rat hearts (expressed as absolute values).

In FIG. 9, we present concentration-response curves to 4i (Example 17), 3a (Example 1) and 4d (Example 7) on the heart rate of isolated rat hearts (expressed as absolute values). Data are presented as mean±S.E.M.

Figure 10:
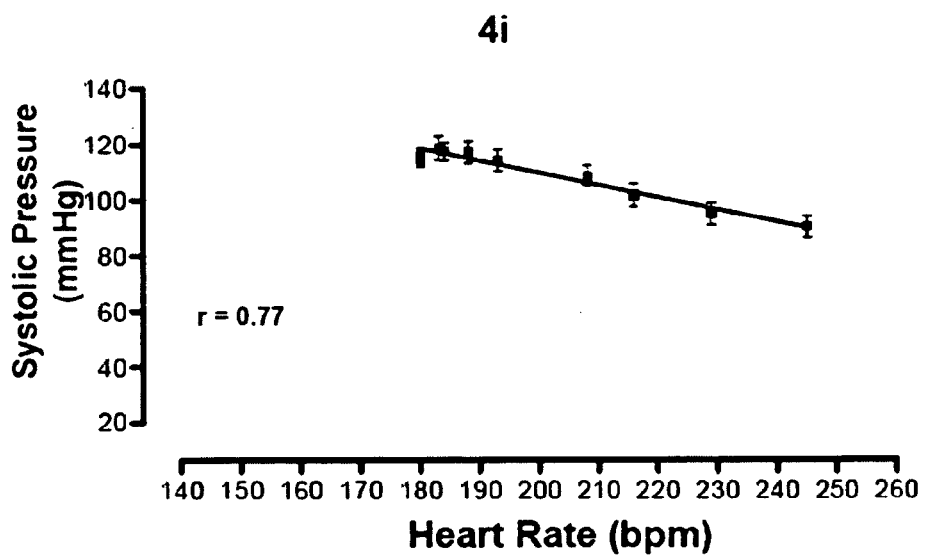
FIG. 10 presents the correlation between ventricular pressure and heart rate, pointing out the existence of an inverse relationship between ventricular pressure and heart rate in the presence of growing doses of compound 4i (Example 17).

In all concentration-response experiments of compounds 4i (Example 17), 3a (Example 1) and 4d (Example 7) in isolated hearts, we observed an increase in systolic pressure of the left ventricle with simultaneous decrease in heart rate, both dependent on compound concentration on perfusion buffer. As in hearts isolated and perfused with crystalloid solutions, variations in heart rate may modify oxygen inflow to the myocardium, and consequently its function, it is possible that heart rate decreases per se cause increase of the systolic pressure. In this way, pressor effects observed in response to quinazoline compounds may follow as a result of its bradycardia effect, and not of a direct inotropic stimulus. In order to test this hypothesis, we studied initially if there was a correlation between levels of pressure and heart rate observed with increased doses of 4i (Example 17). In FIG. 10, we represent the correlation between ventricular pressure and heart rate, suggesting an inverse relationship between ventricular pressure and heart rate in the presence of increased doses of compound 4i (Example 17).

Figure 11:
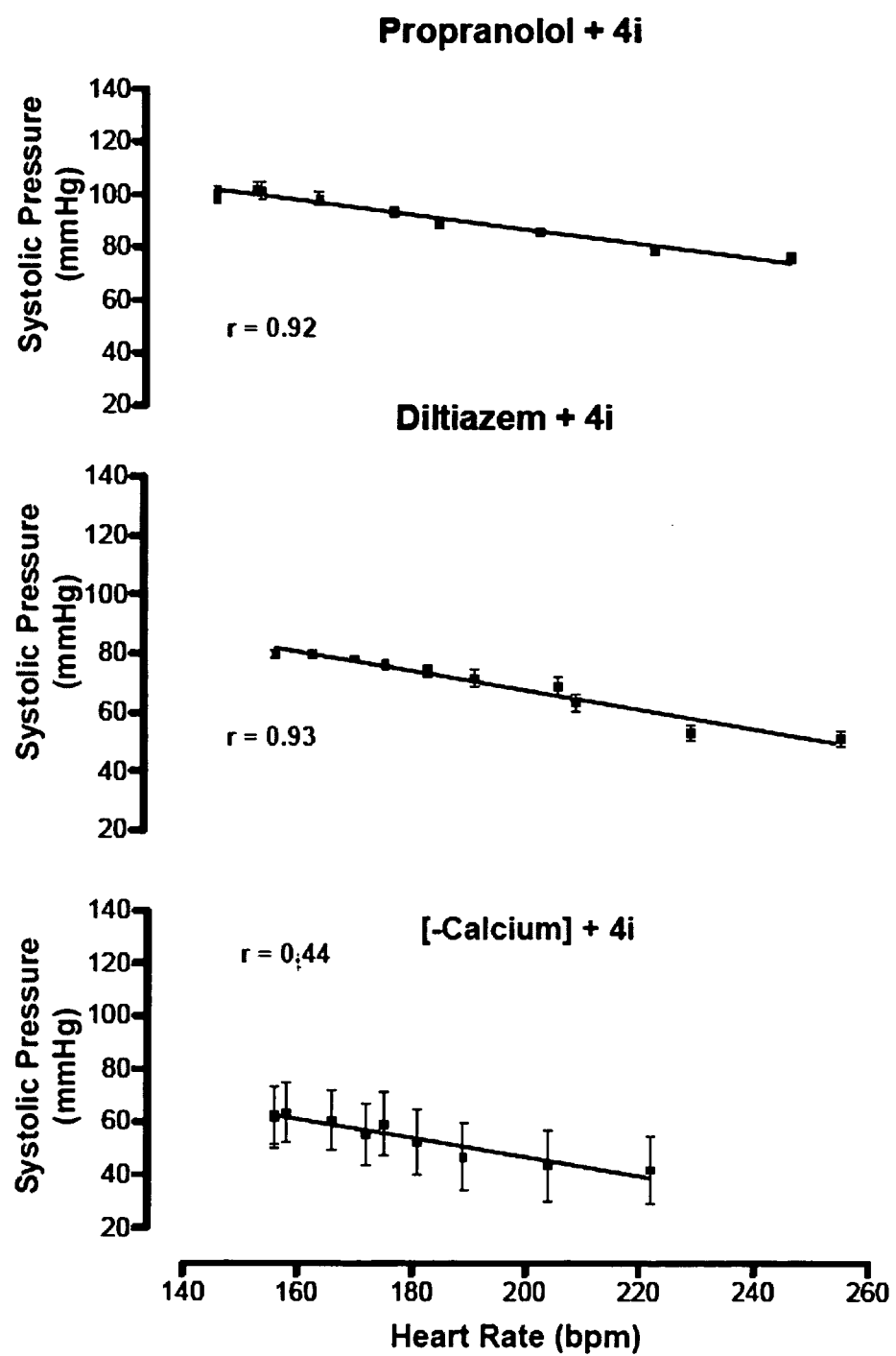
FIG. 11 presents correlation Diagrams between the increase of systolic pressure and decrease in heart rate in isolated hearts submitted to injections (bolus) of 4i (Example 17) perfused with propanolol, diltiazem and with reduction of calcium concentration in the perfusion buffer.

There was also a negative correlation between levels of ventricular pressure and heart rate in isolated hearts treated with increased doses of compound 4i (Example 17) in the presence of blockers like propanolol and diltiazem, and reduced concentrations of calcium in the perfusion buffer. In FIG. 11, we presented diagrams of the correlation between increase in systolic pressure and decrease in heart rate in isolated hearts submitted to injections (bolus) of 4i (Example 17) perfused with propanolol, diltiazem and with reduction of the calcium concentration in the perfusion buffer. Data are presented as mean±S.E.M.

Figure 12:
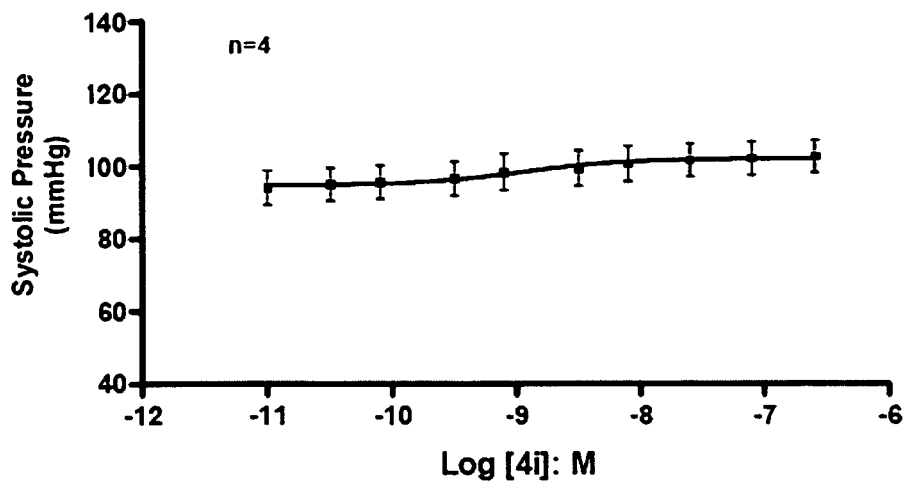
FIG. 12 presents the concentration-response relationship for 4i (Example 17) in an isolated heart submitted to electrical stimulus.

In order to confirm our hypothesis that pressor response of compound 4i depends on bradycardia and not on a direct action of 4i in the inotropism of isolated rat hearts, we conducted experiments where heart rate was held constant during infusion of increased concentrations of 4i (Example 17), through the action of an electrical stimulator. In FIG. 12 we represent the concentration-response relationship to 4i (Example 17) in isolated heart submitted to electrical stimulus. The control of heart rate almost annulled the pressor response to 4i (Example 17).

Figure 13:
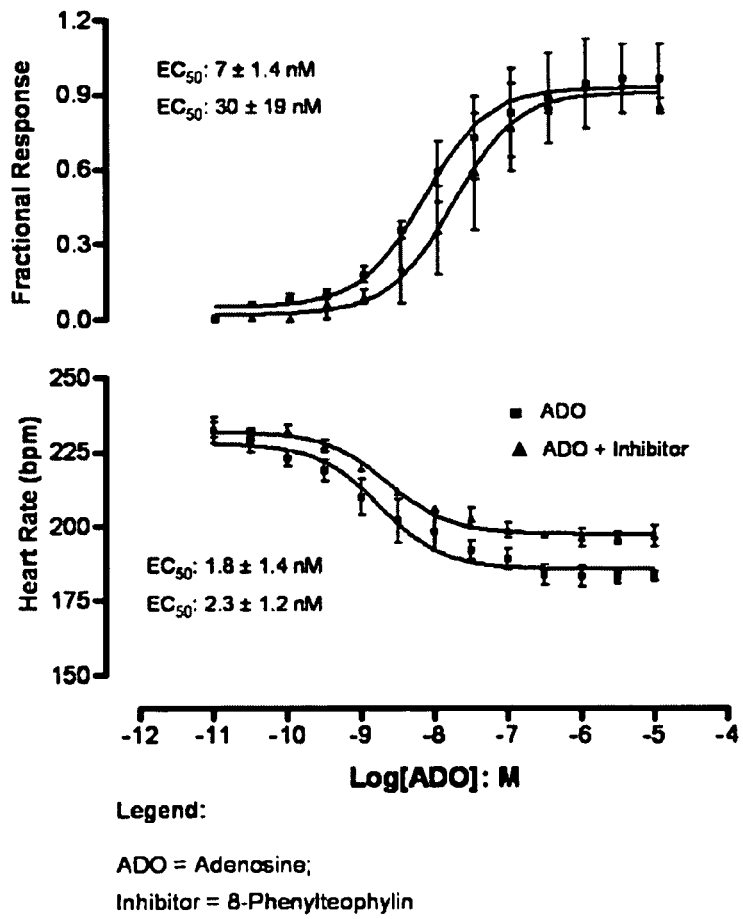
FIG. 13 presents experiments of the concentration-response kind with adenosine and the specific inhibitor of its receptor (8-phenylteophylin-8-FT).

Results obtained with 4i (Example 17) and other quinazoline compounds point out that the main functional effect of these compounds on isolated rat hearts is bradycardia, and the pressor effect depends on bradycardia, and thus is a consequence of particularities of the preparation used (i.e., isolated heart) and not a direct effect. Because the bradycardia response was not altered by propanolol or diltiazem blocking, or even by decrease in calcium concentration in the perfusion buffer, our hypothesis is that this effect of quinazoline compounds depends on a direct effect of them on pacemaker cells, or even on an indirect effect through secretion of autocrine or paracrine compounds. One of the likely responsibles for these effects is adenosine, a compound produced endogenously by myocardic cells, which produces effects, in isolated hearts, similar to those observed with quinazoline compounds (i.e., bradycardia and increase of systolic pressure of the left ventricle). In order to confirm our hypothesis, we conducted concentration-effect experiments with adenosine and the unspecific inhibitor of its receptor (8-phenyltheophylline—8-PT), which demonstrated, as indicated in FIG. 13, that adenosine produced an increase of 16±2 mmHg in the ventricular pressure of isolated hearts, and reduction of approximately 19% in heart rate, compared to absolute basal values, in the concentration of 1 µM of adenosine (maximum response).

$EC_{50}$ value for adenosine pressor response was 7.0±1.4 nM, and for bradycardia response was 1.8±1.4 nM. In Table 3, we present values of $E_{max}$, $EC_{50}$ (nM) and $LogEC_{50}$ in the fractional pressor response to infusion of increased concentrations of adenosine in isolated hearts perfused with pure HEPES buffer, or with HEPES buffer with 8-PT (mean±S.E.M.).

Both effects were altered by the action of the unspecific adenosine receptor inhibitor, 8-PT (1 µM), added to the perfusion buffer. According to results presented in FIG. 13, the increase in systolic pressure in response to infusion of increased concentrations of adenosine, both in control hearts as in those treated with the unspecific adenosine inhibitor, was almost the same. Nevertheless, when the inhibitor was present, there was a shift of the $EC_{50}$ value to the left, presenting the new value of 30±19 nM (Table 3). Concerning heart rate, the adenosine bradycardia effect was reduced when the inhibitor was present, showing a decrease of about 15% if compared to basal values of Table 4, where we present initial and final heart rate values (bpm) in the response to infusion of increased concentrations of adenosine in isolated hearts perfused with pure HEPES buffer and HEPES buffer with 8-PT (mean±S.E.M.).

TABLE 3

|  | Adenosine | Adenosine + 8-PT |
|---|---|---|
| $E_{max}$ | 0.93 ± 0.05 | 0.91 ± 0.04 |
| $EC_{50}$ | 7.0 ± 1.4 | 30 ± 19 |
| $LogEC_{50}$ | −8.2 ± 0.2 | −7.8 ± 0.1 |

TABLE 4

|  | Adenosine | Adenosine + 8-PT |
|---|---|---|
| Initial Heart Rate | 228 ± 2 | 232 ± 1 |
| Final Heart Rate | 185 ± 2 | 197 ± 1 |

Figure 14:
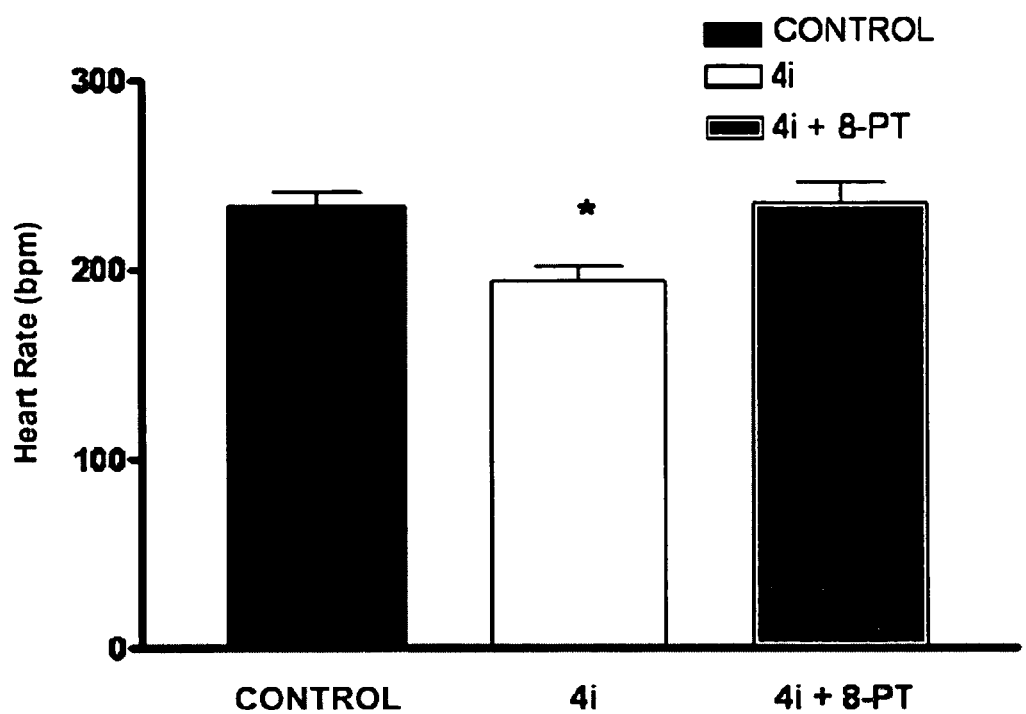
FIG. 14 presents representative heart rate diagrams of isolated rat hearts perfused with pure HEPES buffer (control) or HEPES buffer with 1 nM of 4i (Example 17) plus 1 μM of an specific inhibitor of adenosine receptors, 8-PT (4i+8-PT).

In FIG. 14, we present diagrams that represent heart rates of isolated rat hearts perfused with pure HEPES buffer (control), or HEPES buffer with 1 nM of 4i (Example 17), or HEPES buffer with 1 nM of 4i (Example 17) plus 1 µM of unspecific inhibitor of adenosine receptors, 8-PT (4i+8-PT). Data are presented as mean±S.E.M. for four experiments. *$p<0.05$ compared to the control, and demonstrated that perfusion of hearts with 4i (Example 17) reduces heart rate in approximately 17%, if compared to heart rate values of control hearts. However, perfusion of hearts with 4i (Example 17) and 8-PT annulled bradycardia caused by 4i (Example 17), confirming our hypothesis that the quinazoline compound could be acting in a direct or indirect way on adenosine receptors. In Table 5, we present heart rate values (bpm) from individual experiments of isolated hearts perfused with pure HEPES buffer (control), HEPES buffer with 1 nM of 4i (Example 17), or HEPES buffer with 1 nM of 4i (Example 17) and 1 PM of 8-PT (mean±S.E.M.).

TABLE 5

|  | Control | 4i (Example 17) (1 nM) | 4i (Example 17) (1 nM) + 8-PT |
|---|---|---|---|
| Heart Rate | 233 ± 7 | 194 ± 7 | 234 ± 11 |

What is claimed is:

1. A compound having the formula:

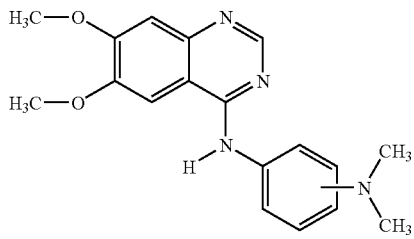

or a pharmaceutically acceptable salt thereof, which inhibits the enzyme adenosine kinase.

2. The compound according to claim 1 which is 6,7-dimethoxy-4-(3'-dimethylaminoanilino)quinazoline.

3. The compound according to claim 1 which is 6,7-dimethoxy-4-(4'-dimethylaminoanilino)quinazoline.

4. The compound according to claim 2 which is in the form of hydrochloride salts.

5. The compound according to claim 3 which is in the form of hydrochloride salts.

6. A pharmaceutical composition comprising a therapeutically effective amount of a compound according to claim 2 in combination with a pharmaceutically acceptable carrier.

7. A pharmaceutical composition comprising a therapeutically effective amount of a compound according to claim 3 in combination with a pharmaceutically acceptable carrier.

* * * * *

UNITED STATES PATENT AND TRADEMARK OFFICE
CERTIFICATE OF CORRECTION

PATENT NO. : 8,513,267 B2  
APPLICATION NO. : 11/515514  
DATED : August 20, 2013  
INVENTOR(S) : Kleber Gomes Franchini et al.

Page 1 of 1

It is certified that error appears in the above-identified patent and that said Letters Patent is hereby corrected as shown below:

ON THE TITLE PAGE:

At item (30), Foreign Application Priority Data, change:

"Feb. 3, 2004 (BR) .................. 0400869" to

--Mar. 2, 2004 (BR) .................. 0400869-3--.

Signed and Sealed this  
Twenty-fourth Day of December, 2013

Margaret A. Focarino  
*Commissioner for Patents of the United States Patent and Trademark Office*